(12) United States Patent
Plasterk

(10) Patent No.: US 12,391,736 B2
(45) Date of Patent: Aug. 19, 2025

(54) OFF-THE-SHELF CANCER VACCINES

(71) Applicant: CureVac Netherlands B.V., Amsterdam (NL)

(72) Inventor: Ronald Hans Anton Plasterk, Amsterdam (NL)

(73) Assignee: CureVac Netherlands B.V., Amsterdam (NL)

( * ) Notice: Subject to any disclaimer, the term of this patent is extended or adjusted under 35 U.S.C. 154(b) by 1147 days.

(21) Appl. No.: 17/262,917

(22) PCT Filed: Jul. 25, 2019

(86) PCT No.: PCT/NL2019/050491
§ 371 (c)(1),
(2) Date: Jan. 25, 2021

(87) PCT Pub. No.: WO2020/022898
PCT Pub. Date: Jan. 30, 2020

(65) Prior Publication Data
US 2021/0238244 A1  Aug. 5, 2021

(30) Foreign Application Priority Data

Jul. 26, 2018 (NL) .................................... 2021400
Jan. 24, 2019 (NL) .................................... 2022447

(51) Int. Cl.
| | |
|---|---|
| *C07K 14/47* | (2006.01) |
| *A61K 39/00* | (2006.01) |
| *C07K 5/083* | (2006.01) |
| *C07K 7/08* | (2006.01) |
| *C12Q 1/6886* | (2018.01) |

(52) U.S. Cl.
CPC ...... *C07K 14/4748* (2013.01); *A61K 39/0011* (2013.01); *A61K 39/001151* (2018.08); *C07K 5/0808* (2013.01); *C07K 7/08* (2013.01); *C12Q 1/6886* (2013.01); *A61K 39/00* (2013.01); *A61K 2039/645* (2013.01); *C07K 2319/00* (2013.01); *C12Q 2600/156* (2013.01)

(58) Field of Classification Search
CPC .... C07K 14/4748; C07K 5/0808; C07K 7/08; C07K 2319/00; A61K 39/0011; A61K 39/001151; A61K 39/00; A61K 2039/645; A61K 2039/70; C12Q 1/6886; C12Q 2600/156
See application file for complete search history.

(56) References Cited

U.S. PATENT DOCUMENTS

| | | |
|---|---|---|
| 9,115,390 B2 | 8/2015 | Liss et al. |
| 2005/0112134 A1 | 5/2005 | Graddis et al. |
| 2007/0083334 A1 | 4/2007 | Mintz et al. |
| 2016/0069895 A1 | 3/2016 | Delamarre et al. |
| 2016/0101170 A1 | 4/2016 | Hacohen et al. |
| 2017/0028043 A1 | 2/2017 | Benz et al. |
| 2017/0028044 A1 | 2/2017 | Soon-Shiong et al. |
| 2017/0032082 A1 | 2/2017 | Nguyen et al. |
| 2017/0032103 A1 | 2/2017 | Nguyen et al. |
| 2017/0202939 A1 | 7/2017 | Carreno et al. |
| 2017/0312351 A1 | 11/2017 | Niazi et al. |
| 2018/0064793 A1 | 3/2018 | Mcgranahan et al. |
| 2018/0078624 A1 | 3/2018 | Zhou et al. |
| 2018/0078625 A1 | 3/2018 | Moon et al. |
| 2018/0318409 A1 | 11/2018 | Valiante et al. |
| 2018/0340944 A1 | 11/2018 | Han et al. |
| 2019/0022202 A1 | 1/2019 | Granum et al. |
| 2019/0030147 A1 | 1/2019 | Artomov et al. |
| 2019/0060428 A1 | 2/2019 | Fritsch |
| 2019/0083593 A1 | 3/2019 | Sahin et al. |
| 2019/0091316 A1 | 3/2019 | Soon-Shiong et al. |

FOREIGN PATENT DOCUMENTS

| | | | |
|---|---|---|---|
| EP | 2071334 A1 * | 6/2009 | ............. C07K 16/32 |
| WO | 1995032731 A2 | 12/1995 | |
| WO | 20040111075 A2 | 12/2004 | |
| WO | 2007101227 A8 | 9/2007 | |
| WO | 2011143656 A2 | 11/2011 | |
| WO | 2012159754 A2 | 11/2012 | |
| WO | 2014168874 A2 | 10/2014 | |
| WO | 2015095811 A2 | 6/2015 | |
| WO | 2016040900 A1 | 3/2016 | |
| WO | 2016154544 A1 | 9/2016 | |
| WO | 2016172722 A1 | 10/2016 | |

(Continued)

OTHER PUBLICATIONS

NLM, "*Homo sapiens* cyclin-dependent kinase inhibitor 1A (p21, Cip1) (CDKN1A), transcript variant 1, mRNA"; URL= https://www.ncbi.nlm.nih.gov/nuccore/NM_000389.2 ; Date= Feb. 24, 2008; Accessed Nov. 2, 2024 (Year: 2008).*

Rajasagi, M. et al., "Systematic identification of personal tumor-specific neoantigens in chronic lymphocytic leukemia", Blood, 2014; 124(3):453-462; ISSN 0006-4971.

Roudko, V. et al., "Widespread immunogenic poly-epitope frameshift mutations in microsatellite unstable tumors", bioRxiv 2019; doi: https://doi.org/10.1101/662262; pp. 1-53.

(Continued)

*Primary Examiner* — Anne M. Gussow
*Assistant Examiner* — Sydney Van Druff
(74) *Attorney, Agent, or Firm* — Verrill Dana, LLP

(57) ABSTRACT

The present invention relates generally to peptide comprising two or more tumor specific neo open-reading-frame peptides (NOPs), and isolated nucleic acids encoding such peptides, and the uses of these peptides and/or isolated nucleic acids to produce cancer vaccines and the like. With the present invention it becomes possible to provide off-the-shelf cancer vaccines and the like within a short period of time and for potentially 30% of the total population of patients suffering from cancer.

3 Claims, 6 Drawing Sheets
Specification includes a Sequence Listing.

(56) References Cited

FOREIGN PATENT DOCUMENTS

| | | | |
|---|---|---|---|
| WO | 2016187508 A2 | 11/2016 | |
| WO | 2016201049 A2 | 12/2016 | |
| WO | 2017020026 A1 | 2/2017 | |
| WO | 2017106638 A1 | 6/2017 | |
| WO | 2017118702 A1 | 7/2017 | |
| WO | 2017132547 A1 | 8/2017 | |
| WO | 2017139694 A1 | 8/2017 | |
| WO | 2017173321 A1 | 10/2017 | |
| WO | 2017177207 A1 | 10/2017 | |
| WO | 2017194170 A1 | 11/2017 | |
| WO | 2017223085 A2 | 12/2017 | |
| WO | 2018015433 A2 | 1/2018 | |
| WO | 2018026896 A1 | 2/2018 | |
| WO | 2018102584 A1 | 6/2018 | |
| WO | 2018136664 A1 | 7/2018 | |
| WO | 2018144082 A1 | 8/2018 | |
| WO | 2018144775 A1 | 8/2018 | |
| WO | 2018195357 A1 | 10/2018 | |
| WO | 2018200389 A1 | 11/2018 | |
| WO | 2018213803 A1 | 11/2018 | |
| WO | 2018223092 A1 | 12/2018 | |
| WO | 2018223094 A1 | 12/2018 | |
| WO | 2018224405 A1 | 12/2018 | |
| WO | 2018234506 A2 | 12/2018 | |
| WO | 2018234516 A2 | 12/2018 | |
| WO | 2019008364 A1 | 1/2019 | |
| WO | 2019008365 A1 | 1/2019 | |
| WO | WO-2019012082 A1 * | 1/2019 | ............ A61K 38/04 |
| WO | 2019036043 A2 | 2/2019 | |

OTHER PUBLICATIONS

Luhui, S. et al., "Abstract 469: Progress towards developing a universal, prophylactic cancer vaccine.", American Association for Cancer Research; vol. 73, No. 8, Suppl. 1, Apr. 2013 (Apr. 1, 2013).

Schwitalle, Y. et al., "Immunogenic peptides generated by frameshift mutations in DNA mismatch repair-deficient cancer cells", Cancer Immun. 2004 Academy of Cancer Immunology, CH-ISSN 1424-9734, vol. 4, Nr:1, pp. 1-10.

Koster, J. et al., "A library of Neo Open Reading Frame peptides (NOPs) as a sustainable resource of common neoantigens in up to 50% of cancer patients", Scientific Reports, 2019, vol. 9, Nr: 1.

Zhang, J. et al., "Using Frameshift Peptide Arrays for Cancer Neo-Antigens Screening", Scientific Reports, vol. 8, No. 1, (2018), pp. 1-10.

Batista, M. T. et al., "Abstract 1463: FAST vaccines based on frameshift neoantigens may have advantages over personal vaccines", Proceedings of American Association for Cancer Research Annual Meeting 2019, Mar. 29, 2019, vol. 79, Nr.: 13, pp. 1-2.

Orfanelli, T. et al., "Shared tumor antigens in uterine cancers with microsatellite instability: Putative targets for immunotherapeutic approaches", Gynecologic Oncology, Jun. 2019, 154(1):91, DOI: 10.1016/j.ygyno.2019.04.214.

Linnebacher et al., "Frameshift peptide-derived T-cell epitopes: a source of novel tumor-specific antigens", Int. J. Cancer: 93, pp. 6-11 (2001).

Schumacher et al., "Neoantigens in cancer immunotherapy", Science, 2015, vol. 348, Issue 6230, pp. 69-74.

Rahma et al., "A pilot clinical trial testing mutant von Hippel-Lindau peptide as a novel immune therapy in metastatic Renal Cell Carcinoma", Journal of Translational Medicine, 2010, 8:8, 9 pages.

Hacohen et al., "Getting Personal with Neoantigen-Based Therapeutic Cancer Vaccines", Cancer Immunol. Res., Jul. 2013; 1(1): 11-15, pp. 1-8.

Ito et al., "Cancer Neoantigens: A Promising Source of Immunogens for Cancer Immunotherapy", J Clin Cell Immunol 2015, 6:2, pp. 1-7.

Tomczak et al., "The Cancer Genome Atlas (TCGA): an immeasurable source of knowledge", Contemp Oncol (Pozn). 2015, 19 (1A): A68-A77.

The Cancer Genome Atlas Research Network. "Comprehensive molecular characterization of clear cell renal cell carcinoma", Nature (2013), 499, pp. 43-49.

Pavlopoulou et al., "Human cancer databases (review)", Oncology Reports, 33: pp. 3-18, 2015.

Rammensee, H-G et al., "Cancer Vaccines: Some Basic Considerations", Genomic and Personalized Medicine, 2009, Elsevier, pp. 573-589.

* cited by examiner

Normal protein

Protein with NOP in patient with frame shift mutation

Potential NOPs

OFF-THE-SHELF CANCER VACCINES

FIELD OF THE INVENTION

The present invention relates generally to vaccines for use in the treatment of cancer, wherein a vaccine is based on combining multiple tumor specific neo open-reading-frame peptides (NOPs) sequences in a single vaccine, preferably wherein said NOPs are derived from the same gene. The invention further relates to peptides comprising such sequences, nucleic acids encoding such peptides and methods for constructing such peptides, nucleic acids and vaccines.

BACKGROUND OF THE INVENTION

There are a number of different existing cancer therapies, including ablation techniques (e.g., surgical procedures and radiation) and chemical techniques (e.g., pharmaceutical agents and antibodies), and various combinations of such techniques. Despite intensive research such therapies are still frequently associated with serious risk, adverse or toxic side effects, as well as varying efficacy.

There is a growing interest in cancer therapies that aim to target cancer cells with a patient's own immune system (cancer vaccines). Such therapies may indeed eliminate some of the known disadvantages of existing therapies, or be used in addition to the existing therapies for additional therapeutic effect. Cancer vaccines or immunogenic compositions intended to treat an existing cancer by strengthening the body's natural defenses against the cancer and based on tumor-specific neoantigens hold great promise as next-generation of personalized cancer immunotherapy. Evidence shows that such neoantigen-based vaccination can elicit T-cell responses and can cause tumor regression in patients.

Typically the immunogenic compositions/vaccines are composed of tumor antigens (antigenic peptides or nucleic acids encoding them) and may include immune stimulatory molecules like cytokines and that work together to induce antigen-specific cytotoxic T-cells that target and destroy tumor cells. Vaccines containing tumor-specific and patient-specific neoantigens requires sequencing of the patients' genome, as well as the production of personalized compositions. Sequencing, identifying the patient's specific neoantigens and preparing such personalized compositions may require a substantial amount of time, time which may unfortunately not be available to the patient, given that for some tumors the average survival time after diagnosis is short, sometimes around a year or less.

Accordingly, there is a need for improved methods and compositions for providing subject-specific immunogenic compositions/cancer vaccines. In particular it would be desirable to have available a vaccine for use in the treatment of cancer, wherein such vaccine is suitable for treatment of a larger number of patients, and can thus be prepared in advance and provided off the shelf.

In light of this, products, compositions, systems, methods and uses that provide for vaccines for use in the treatment of cancer and that would take away some of the herein-described disadvantages would be highly desirable, but are not yet readily available. In particular there is a clear need in the art for off-the-shelf personalized vaccines which induce an immune response to tumor specific neo antigens. Accordingly, the technical problem underlying the present invention can be seen in the provision of such products, compositions, methods and uses for complying with any of the aforementioned needs.

The technical problem is solved by the embodiments characterized in the claims and herein below.

SUMMARY OF THE INVENTION

It is an aim of the present invention to provide for an off-the-shelf vaccine for the treatment of cancer in a subject.

It is an aim of the present invention to provide for an off-the-self vaccine wherein the vaccine comprises a peptide or protein, or a nucleic acid encoding such peptide or protein, the peptide or protein comprising at least two amino acid sequences that have been found in tumors in cancer patients, or encoded by genomes of the cancer cells in such cancer patients, and that are the consequence of frame-shift mutations that have been introduced in the genome of the cancer cells of cancer patients. The amino acid sequences are preferably selected from the sequences identified with SEQ ID Nos 1-4307.

It is an aim of the present invention to provide for an off-the-self vaccine wherein the vaccine comprises a peptide or protein, or a nucleic acid encoding such peptide or protein, the peptide or protein comprising all amino acid sequences that have been found in tumors in cancer patients, or encoded by genomes of the cancer cells in such cancer patients, and that are the consequence of frame-shift mutations that have been introduced in one and the same gene in the genome of the cancer cells of cancer patients. The genes and amino acid sequences are preferably selected from the genes identified as groups 1-1103 in Table 1, and the accompanying SEQ ID nos. per gene.

By identifying in a cancer patient the genes as disclosed herein and that have been hit by frameshift mutations causing the genome of the cancer cells to encode for peptides comprising the amino acid sequences as disclosed herein, the patient can be provided with, depending on the number of genes that have been hit with such frameshift mutation, one, two or more peptides according to the invention, wherein a first peptide comprises for a first hit gene (i.e. a first group in Table 1) at least two, preferably all, of the corresponding amino acid sequences as indicated in Table 1 (or an isolated nucleic acid encoding such peptide), a second peptide comprises for a second hit gene (i.e. a second group in Table 1) at least two, preferably all, of the corresponding amino acid sequences as indicated in Table 1 (or an isolated nucleic acid encoding such peptide), and so on.

It is also an aim of the present invention to provide for an off-the-self vaccine wherein the vaccine comprises a peptide or protein, or a nucleic acid encoding such peptide or protein, the peptide or protein comprising at least two amino acid sequences that are also present in the tumor of the patient, or encoded by the genome of the cancer cells, and that are the consequence of frame-shift mutations that have been introduced in the genome of the cancer cells.

It is an aim of the current invention that the peptide or protein comprising all amino acid sequences that are also present in the tumor of the patient, or encoded by the genome of the cancer cells, and that are the consequence of frame-shift mutations that have been introduced in the genome of the cancer cells. By providing one peptide or protein, or nucleic acid encoding such protein or peptide, comprising all such amino acid sequences, it has now become possible to treat a cancer patient with one vaccine and that comprises all amino acid sequences that are unique to the cancer cell as the consequence of frame-shift mutations that are present in the genome of the cancer patient. Preferably all the amino acid sequences that are present in the tumor of a patient are selected from the group consisting of SEQ ID Nos 1 to 4307.

It is an aim of the present invention to provide for a peptide comprising at least two amino acid sequences, wherein each of said amino acid sequence is independently selected from the group consisting of SEQ ID Nos 1 to 4307.

It is a further objective of the present invention to provide for an isolated nucleic acid comprising a nucleotide sequence encoding said peptide.

It is a further objective of the present invention to provide for a vector comprising said isolated nucleic acid.

It is a further objective of the present invention to provide for an expression vector comprising a promoter operably linked to said isolated nucleic acid.

It is a further objective of the present invention to provide for a host cell comprising said isolated nucleic acid.

It is a further objective of the present invention to provide for a vaccine comprising said peptide, or said isolated nucleic acid, or said vector, or said expression vector, optionally further comprising a pharmaceutically acceptable excipient.

It is a further objective of the present invention to provide for said vaccine for use in the prevention or treatment of a disease, preferably wherein said disease is cancer.

It is a further objective of the present invention to provide for a library comprising 2, 3, 4, 5, 6, 7, 8, 9, 10, 20, 30, or more vaccines according to the invention, each vaccine individually comprising at least two, preferably all, amino acid sequences selected from a group selected from the groups 1-1103 as listed in Table 1, or a nucleotide sequence encoding said amino acid sequences, and wherein said 2, 3, 4, 5, 6, 7, 8, 9, 10, 20, 30, or more vaccines each comprise amino acid sequences, or nucleotide sequences encoding said amino acid sequences, from a different group selected from the groups of sequences listed in Table 1.

It is a further objective of the present invention to provide for a method for generating a nucleic acid coding for a peptide, the method comprising the steps of:
  a) identifying frame shift mutations in the tumor DNA and/or RNA of a cohort of cancer patients in order to obtain a frame shift library;
  b) identifying at least one gene which is changed by a frame shift mutation in the tumor DNA and/or RNA of one or more patients in the cohort of cancer patients to obtain a frame shift gene;
  c) identifying each novel open reading frame in both the +1 and −1 reading frame that overlaps with or is adjacent to the frame shift location of the frame shifted gene to obtain candidate novel open reading frame sequences;
  d) optionally when present, identifying each novel open reading frames in both the +1 and −1 reading frame that overlaps with or is adjacent to the frame shift location for each alternative splicing construct of the frame shift gene to obtain candidate novel alternative splicing open reading frame sequences;
  e) combining each of the candidate open reading frame sequences and optionally the candidate novel alternative splicing open reading frame sequences of the frame shift gene in a nucleic acid construct.

This and other objectives are provided by the peptides, isolated nucleic acids, vectors, expression vectors, host cells, vaccines, vaccine compositions, compositions for use and methods as defined throughout the description and as defined in the claims.

BRIEF DESCRIPTION OF THE DRAWINGS

Embodiments of the invention are further described hereinafter with reference to the accompanying drawings, in which.

REFERENCE TO A SEQUENCE LISTING

Figure 1:
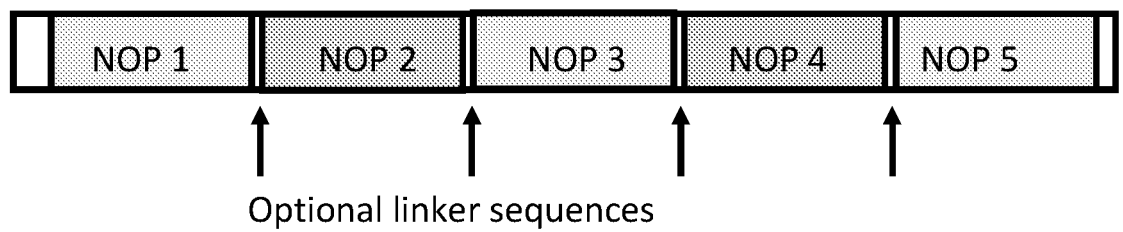
FIG. 1: Schematic overview of a polyNOP peptide, an example of a peptide according to the invention and comprising multiple NOP amino acid sequences which are optionally linked by an amino acid linker sequence, as indicated.
Figure 2:
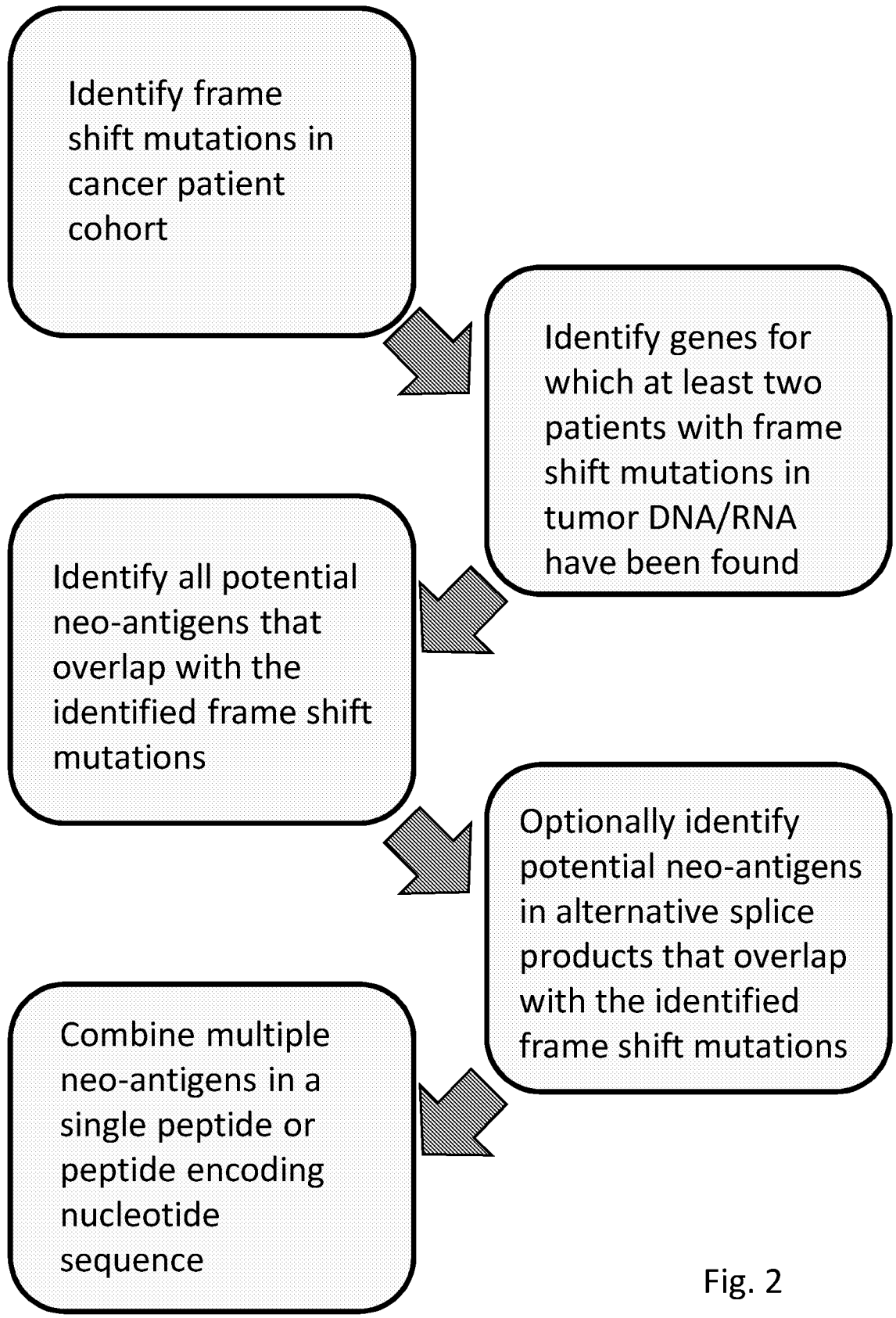
FIG. 2: Schematic overview of a method according to the invention to select candidate NOPs and subsequent construction of a polyNOP peptide according to the invention.

The Sequence listing, which is a part of the present disclosure, includes a text file comprising amino acid sequences of the present invention. The subject matter of the Sequence listing is incorporated herein by reference in its entirety. The information recorded in computer readable form is identical to the written sequence listing.

DEFINITIONS

The section headings used herein are for organizational purposes only and are not to be construed as limiting the subject matter described.

A portion of this disclosure contains material that is subject to copyright protection (such as, but not limited to, diagrams, device photographs, or any other aspects of this submission for which copyright protection is or may be available in any jurisdiction). The copyright owner has no objection to the facsimile reproduction by anyone of the patent document or patent disclosure, as it appears in the Patent Office patent file or records, but otherwise reserves all copyright rights whatsoever.

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

For purposes of the present invention, the following terms are defined below.

The singular form terms "A," "an," and "the" include plural referents unless the content clearly dictates otherwise. Thus, for example, reference to "a cell" includes a combination of two or more cells, and the like.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "and/or" refers to a situation wherein one or more of the stated cases may occur, alone or in combination with at least one of the stated cases, up to with all of the stated cases.

As used herein, the term "at least" a particular value means that particular value or more. For example, "at least 2" is understood to be the same as "2 or more" i.e., 2, 3, 4, 5, 6, 7, 8, 9, 10, 11, 12, 13, 14, 15 . . . etc. As used herein, the term "at most" a particular value means that particular value or less. For example, "at most 5" is understood to be the same as "5 or less" i.e., 5, 4, 3 . . . −10, −11, etc.

The term "comprising" is construed as being inclusive and open ended, and not exclusive. Specifically, the term and variations thereof mean the specified features, steps or components are included. These terms are not to be interpreted to exclude the presence of other features, steps or components. It also encompasses the more limiting "to consist of".

"Exemplary" means "serving as an example, instance, or illustration," and should not be construed as excluding other configurations disclosed herein.

As used herein, administration or administering in the context of treatment or therapy of a subject is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

As used herein, "therapy" or "treatment" refers to treatment of a tumor with a therapeutic substance. A treatment may involve administration of more than one substance. A substance may be administered alone or in combination with other treatments, either simultaneously or sequentially dependent upon the condition to be treated. For example, the therapy may be a co-therapy involving administration of two agents, one or more of which may be intended to treat the tumor. The substances may be administered simultaneously, separately, or sequentially which may allow the agents to be present in the patient requiring treatment at the same time and thereby provide a combined therapeutic effect, which may be additive or synergistic. The therapy may be administered by one or more routes of administration, e.g. parenteral, intra-arterial injection or infusion, intravenous injection or infusion, intraperitoneal, intratumoral or oral. The therapy may be administered according to a treatment regime. The treatment regime may be a pre-determined timetable, plan, scheme or schedule of therapy administration which may be prepared by a physician or medical practitioner and may be tailored to suit the patient requiring treatment. The treatment regime may indicate one or more of: the type of therapy to administer to the patient; the dose of each drug; the time interval between administrations; the length of each treatment; the number and nature of any treatment holidays, if any etc. For a co-therapy a single treatment regime may be provided which indicates how each drug/agent is to be administered.

This term "cancer" refers to the physiological condition in mammals that is typically characterized by unregulated cell growth. The terms "cancer," "neoplasm," and "tumor," are often used interchangeably to describe cells that have undergone a malignant transformation that makes them pathological to the host organism. Primary cancer cells can be distinguished from non-cancerous cells by techniques known to the skilled person. A cancer cell, as used herein, includes not only primary cancer cells, but also cancer cells derived from such primary cancer cell, including metastasized cancer cells, and cell lines derived from cancer cells. Examples include solid tumors and non-solid tumors or blood tumors. Examples of cancers include, without limitation, leukemia, lymphoma, sarcomas and carcinomas (e.g. colon cancer, pancreatic cancer, breast cancer, ovarian cancer, glioblastoma, prostate cancer, lung cancer, melanoma, lymphoma, non-Hodgkin lymphoma, colon cancer, (malignant) melanoma, thyroid cancer, papillary thyroid carcinoma, lung cancer, non-small cell lung carcinoma, and adenocarcinoma of lung). As is well known, tumors may metastasize from a first locus to one or more other body tissues or sites. Reference to treatment for a "neoplasm, "tumors" or "cancer" in a patient includes treatment of the primary cancer, and, where appropriate, treatment of metastases.

As used herein the term "antigen" is a substance, preferably a (poly) peptide that induces an immune response.

As used herein the term "neoantigen" or "neoantigenic peptide" is an antigen that has at least one alteration that makes it distinct from the corresponding wild-type, parental antigen, e.g., via mutation in a tumor cell. A neoantigen can include a polypeptide sequence or a nucleotide sequence. The term "neoantigenic peptide" also encompasses a nucleotide sequence encoding such neoantigen peptide. A tumor neoantigen" or "tumor-specific neoantigen" is a neoantigen present in a subject's tumor cell or tissue but not in the subject's corresponding normal cell or tissue. The neoantigen of the present invention are tumor-specific neoantigens.

As used herein the term "epitope" is the specific portion of an antigen typically bound by an antibody or T cell receptor. As used herein the term "neoepitope" is the specific portion of a neoantigen typically bound by an antibody or T cell receptor.

The term "peptide" is used herein interchangeably with "mutant peptide" and "neoantigenic peptide" to designate a series of residues, typically L-amino acids, connected one to the other, typically by peptide bonds between adjacent amino acids. Similarly, the term "polypeptide" is used interchangeably with "mutant polypeptide" and "neoantigenic polypeptide" in the present specification to designate a series of residues, typically L-amino acids, connected one to the other, typically by peptide bonds between the adjacent amino acids. The polypeptides or peptides can be a variety of lengths. Particularly the term "peptide" is also used for novel amino acid sequences comprising two or more (neoantigenic) peptides, also referred to herein as polyNOP.

In certain embodiments the size of the at least one neoantigenic peptide (NOP) molecule may comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino acid molecule residues, and any range derivable therein. In specific embodiments the neoantigenic peptide molecules are equal to or less than 50 amino acids.

In certain embodiments the size of the at least one peptide according to the invention (polyNOP) may comprise, but is not limited to, about 20, about 21, about 22, about 23, about 24, about 25, about 26, about 27, about 28, about 29, about 30, about 35, about 40, about 45, about 50, about 60, about 70, about 80, about 90, about 100, about 120, about 140, about 160, about 180, about 200, about 250, about 300, about 350, about 400, about 500, about 600, about 700, about 800, about 900, about 1000, about 1100, about 1200, about 1300, about 1400, about 1500, about 1600, about 1700, about 1800, about 1900, about 2000, about 2200, about 2400, about 2600, about 2800, about 3000, about 3500, about 4000, about 4500 or greater amino acid molecule residues, and any range derivable therein. In specific embodiments the peptide according to the invention are equal to or less than 1000 amino acids.

The neoantigens and polypeptides preferably does not induce an autoimmune response and/or invoke immunological tolerance when administered to a subject.

As used herein the term "ORF" means open reading frame. As used herein the term "neoORF" is a tumor-specific ORF arising from a mutation, in particular a frame shift mutation as described herein. A "frame shift mutation" is a mutation causing a change in the frame of the protein, for example as the consequence of an indel mutation as described herein.

Within the context of the current invention the mutation in the tumor cell that gives rise to the neoantigen is a frame shift mutation with a net change of sequence, compared to wildtype, that is not + or − 3 nucleotides or a multiplicity thereof (6, 9, 12, 15 etc.). For example the frame shift consists + or − 1, 2, 4, 5, 7, 8 . . . nucleotides. As will be understood by the skilled person, the frame shift mutation within the context of the current invention and should not create a novel stop triplet on the spot. The frame shift within the context of the current invention gives rise to a neoORF, a novel open reading frame generated in the tumor by insertions, deletions or substitutions that bring in frame sequences encoding completely novel stretches of amino acids. The frame shift mutation within the context of the current invention is a mutation that occurs in the coding region of a gene; i.e. the region that encodes a protein. (Note that the new open reading frame can sometimes extend beyond the stop codon of the wild type gene).

When referring herein to reading frame, the +1 and −1 reading frame mean those reading frames starting at one nucleotide downstream or upstream respectively. It is further to be understood that the −1 reading frame is the same as the +2 reading frame, or the +5 reading frame, etc. Similarly, the +1 reading frame is the same as the −2 reading frame or the +4 reading frame, etc.

As used herein the term "immunogenic" is the ability to elicit an immune response, e.g., via T cells, B cells, or both. As used herein, an immunogenic composition is a composition comprising substances, in particular neoantigen with the ability to elicit an immune response. Such composition may for example be a neoantigen-based vaccine based on one or more neoantigens, e.g., a plurality of neoantigens.

As used herein the term "sequence" can refer to a peptide sequence, DNA sequence or RNA sequence. The term "sequence" will be understood by the skilled person to mean either or any of these, and will be clear in the context provided. For example, when comparing sequences to identify a match, the comparison may be between DNA sequences, RNA sequences or peptide sequences, but also between DNA sequences and peptide sequences. In the latter case the skilled person is capable of first converting such DNA sequence or such peptide sequence into, respectively, a peptide sequence and a DNA sequence in order to make the comparison and to identify the match.

As used herein the term "exome" is a subset of the genome that codes for proteins. An exome can be the collective exons of a genome.

As used herein the term "transcriptome" is the set of all RNA molecules is a cell or population of cells. In a preferred embodiment the transcriptome refers to all mRNA.

As used herein the term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

As used herein the term "subject" encompasses a cell, tissue, or organism, human or non-human, whether in vivo, ex vivo, or in vitro, male or female. The term subject is inclusive of mammals including humans. Preferably the subject is a human subject diagnosed with cancer or suspected to have cancer.

As used herein the term "mammal" encompasses both humans and non-humans and includes but is not limited to humans, non-human primates, canines, felines, murines, bovines, equines, and porcines.

As used herein, we define a NeoORFeome as the set of all sequences in the human genome that are out of frame with known translated genes, but that as a result of a frame shift mutation can become in frame and encode a novel peptide of at least 8 or 10 amino acids in length before encountering a stop codon. The NeoORFeome is the complete space in which by single frame shift mutations novel peptides of significant length (here defined as 10 amino acids or longer) can be encoded and (potentially) expressed. In other words, the NeoORFeome comprises the complete set of neo Open Reading Frame in the human genome, defined as the sum of open reading frames that are not found in frame in the wild type human genome without mutation, but which by a single insertion/deletion/substitution can be made to be in frame, and then encode a peptide of at minimal length 8, 10 amino acids. The human NeoORFeome as here defined in its latest version (in which peptides whose initiations are in the UTR are removed) comprises 25,617,715 amino acids, approximately 26 million. This corresponds to approximately 105 Mb (Megabases) of encoding DNA. (The Human Genome is around 3000 Mb).

We define herein peptides that are not encoded by the wild type human genome, but after frame shift mutation as defined herein, and can be encoded by a tumor genome as a novel open reading frame peptide, or NOP. For any potential NOP in the NeoORFeome the C-terminal sequence is fixed (bounded by the encounter of a stop codon) and not dependent on the precise location of the frame shift mutation; the N-terminus, however, is defined by the mutation site, which is where potentially protein translation shifts into the novel frame. The most upstream novel sequence of a NOP is the most 5' triplet in the wild type human genome of the Neo Open Reading Frame sequence which is not a stop triplet. We define the potential NOPs, also referred to as the pNOPs, as the amino acid sequences encoded by the longest possible sequence, so from the most upstream triplets as described to the stop triplet at the 3' end. Sequences of such potential NOPs are represented in the amino acid sequences as defined herein as NOPs, a selection of potential NOPs is represented by the sequence listing (SEQ ID Nos 1-4307).

Indeed the selection of pNOPs represented by the sequence listing is defined as (part of) the subset of the Neo-Orfeome which we found to be the most frequently switched on by frame shift mutation in a very large set of tumor sequence data; it is thus a listing of potential NOPs or pNOPs. The complete sequence listing (SEQ ID Nos 1-4307) contains pNOPs that are encountered in over 44% of all cancers as described in the TCGA database. Based on our analysis for any new tumor of which the genome (or transcriptome or exome or ORFeome—which is also included in any of the embodiments described below referring to genome, exome or transcriptome) is sequenced, the chance is over 30% that it will encode a NOP that is listed in our library as described here. In other words: the NOPs as provided by the sequence listing (SEQ ID Nos 1-4307) can potentially provide to over 44% of all cancer patients.

As used herein, we define polyNOP as a peptide which comprises at least two NOPs, preferably selected from SEQ ID 1-4307, which NOPS may, within the peptide, be adjacent to each other or be separated by, for example, small amino acid linkers (as will be discussed in more detail herein). As NOPs are defined by out of frame open reading frame peptides which are flanked by stop codons, it logically follows that multiple NOPs combined in one peptide or encoded in a single open reading frame is unlikely to occur in nature. PolyNOPs can for example be constructed by linking multiple NOP encoding nucleic acid sequences, with or without linker sequence, and in the same reading frame, followed by expression of the amino acid sequence encoded by such nucleic acid. It is disclosed herein that polyNOPs according to the invention may comprise two or more NOPs derived from the same gene or two or more NOPs derived from different genes. Preferably a polyNOP comprises 2, 3, 4, 5, 6, 7, 8, 9, 10, 11, 12, 13, 14, 15, 16, 17, 18, 19, 20 or more NOPs, preferably, when the NOPs in a polyNOP are all obtained from the same gene, in a preferred embodiment, the peptide comprises all NOPs as defined herein for said gene.

When used herein, candidate NOP means a NOP which overlaps or is adjacent to a frame shift mutation is defined herein.

As used herein "off-the-shelf" means a vaccine or vaccine composition, e.g. comprising one or more peptides or nucleic acids as defined herein that is available and ready for administration to a patient. For example, when a certain frame shift mutation is identified in a patient, the term "off-the-shelf" would refer to a vaccine according to the invention that is ready for use in the treatment of the patient, meaning that, if the vaccine is peptide based, the corresponding polyNOP peptide may, for example already be expressed and for example stored with the required excipients and stored appropriately, for example at −20° C. or −80° C. Preferably the term "off-the-shelf" also means that the vaccine has been tested, for example for safety or toxicity. More preferably the term also means that the vaccine has also been approved for use in the treatment or prevention in a patient.

As used herein "overlap", when referring to a frame shift mutation to overlap with a NOP or vice versa, means that from all potential NOPs as encoded by the +1 and −1 reading frame for a certain gene, those NOPs are said to overlap with the frame shift location that contain an amino acid sequence that can be encoded by the sequence surrounding the frame shift location in the +1 reading frame and in the −1 reading frame.

For example in case of an insertion, if the non-frame shifted protein is encoded by the sequence: [sequence_1][sequence_2] and encodes the amino acid sequence RHDGCRP, and the frame shift encoding sequence from a patients is [sequence_1]C[sequence_2] (insertion) and encodes the amino acid sequence: RHDALSA, then NOPs that overlap with the frame shift location are the NOP for which a part of the sequence can be encoded by [sequence_1][sequence_2] in reading frame +1 and the NOP for which a part of the sequence can be encoded by [sequence_1][sequence_2] in reading frame-1, for example the NOPs comprising the amino acids sequences VTTAVG and SRRLSA respectively.

For example in case of an deletion, if the non-frame shifted protein is encoded by the sequence: [sequence_1]AT[sequence_2] and encodes the amino acid sequence RHD-GIVG, and the frame shift encoding sequence from a patients is [sequence_1][sequence_2] (deletion) and encodes the amino acid sequence: RHDGCRP, then NOPs that overlap with the frame shift location are the NOP for which a part of the sequence can be encoded by [sequence_1][sequence_2] in reading frame +1 and the NOP for which a part of the sequence can be encoded by [sequence_1][sequence_2] in reading frame-1, for example the NOPs comprising the amino acids sequences VTTALSA and SRRHCRP respectively.

In case the frame shift location is very close or at the border of two neighboring NOPs (for example due to an out of frame stop codon), the NOPs are referred herein as "adjacent", and defined as comprising a stretch of amino acids encoded by nucleotides corresponding to for example 9 consecutive nucleotides, or 10, 11, 12, 13, 14, 15, 16, 17 or 18 consecutive nucleotides, starting from 3 nucleotides upstream or downstream from the location of the frame shift location and which are not defined as overlapping as defined above.

For example, if the non-frame shifted protein is encoded by [sequence_1]GCGCTGT[sequence_2] and the frame shift encoding sequence is [sequence_1]GCGTGT[sequence_2], then the NOPs that comprise an amino acid sequence that can be encoded by either nucleic acid sequence 1 or nucleic acid sequence 2 in either reading frame +1 or reading frame −1 are said to be adjacent, provided they are not already defined as overlapping as defined above.

DETAILED DESCRIPTION

NOP sequences (also referred to as neo Open Reading Frames, neoORFs) have been previously described as potential cancer vaccines. See, for example, WO95/32731, WO2016172722 (Nantomics), WO2016/187508 (Broad), WO2017/173321 (Neon Therapeutics), US2018340944 (University of Connecticut), and WO2019/012082 (Nouscom), as well as Rahma et al. (Journal of Translational Medicine 2010 8:8) which describes peptides resulting from frameshift mutations in the von Hippel-Lindau tumor suppressor gene (VHL) and Rajasagi et al. (Blood 2014 124 (3): 453-462) which reports the systematic identification of personal tumor specific neoantigens.

The present disclosure uses NOP sequences that are shared among cancer patients to generate combinations of NOP sequences. The preferred combinations of NOP sequences, as claimed herein, can be used as off-the-shelf therapeutic vaccines for a large proportion of cancer patients or for prophylactic use. The combination of the specific shared NOP sequences into a single vaccine and the use of the preferred combinations for treatment or prevention of cancer has not been described before in the art.

It is contemplated that any method, use or composition described herein can be implemented with respect to any other method, use or composition described herein. Embodiments discussed in the context of methods, use and/or compositions of the invention may be employed with respect to any other method, use or composition described herein. Thus, an embodiment pertaining to one method, use or composition may be applied to other methods, uses and compositions of the invention as well.

As embodied and broadly described herein, the present invention is directed to the surprising finding that developing a vaccine for neo open reading frame peptides (antigens) from frame shift mutations in relatively few genes are sufficient to develop a potential vaccines for a large percentage of cancer patients.

It was realized by the inventor of the present invention that it is possible to provide a peptide that comprises (sequences of) neo open reading frame peptides that are found in tumor material of patients as the consequence of frame shift mutations that lead to a new open reading frame with a novel, common, tumor-specific protein sequence towards the C-terminal end, preferably comprising two or more sequences as defined in the sequence listing (SEQ ID Nos 1-4307). By comparing sequence information from a tumor sample of a patient with the sequence listing it has now become possible to quickly identify whether there is a match between sequences identified in the patient's material with a sequence in the sequence listing. A match is identified when a sequence identified in the patients material and a sequence from the sequence listing have a string, i.e. a peptide sequence (or RNA or DNA sequence encoding such peptide (sequence) in case the comparison is on the level of RNA or DNA) in common representative of at least 8, preferably at least adjacent amino acids. The thus identified tumor-specific mutant polypeptide encoded by a tumor-specific frame shift mutation in (expressed) genes of the subject having cancer can be used to provide for neoantigens comprising a tumor-specific neoepitope. With these limited amount of sequences, and based on the actual amount of sequences in the sequence listing (as described herein elsewhere) it is estimated that between about 5-30% of the population of patients having cancer can be provided with a subject-specific and tumor-specific immunogenic composition comprising one or more neoantigens based on one or more matches between sequence identified in the patients material and a sequence from the sequence listing.

In some more detail, it was realized by the inventor of the present invention that with the human genome being about $3 \times 10^9$ base pairs, about 1.5% of which is coding for protein, the number of possible point-mutations (nucleotide changes or SNVs) is virtually infinite, especially since each position can mutate into three others, and of course endless other rearrangements and indels are possible. Therefore the number of possible neoantigens that arise in tumors is also huge.

A specific window of cancer mutations is derived from the reference human genome sequence. While the $3 \times 10^9$ base pairs can mutate in infinite ways, there is only a limited repertoire of possible neoantigens dictated by the coding (and expressed) part of the human genome sequence. The ORFeome (the complete set of open reading frames (ORFs) in a genome), as it has been referred to, is 'meant' to be read in the proper reading frame. However, there are two other frames of each gene, the −1 and +1. These alternative frames do not necessarily encode relevant peptides, since they may run into a stop triplet fast. The present inventor has defined that part of the genome that encodes peptides resulting from out of frame translation and that are at least the size of a potential epitope when it is seen as a neoantigen. These peptides are referred to as the neo open reading frame peptides, or NOPs. The maximal coding region for each of these NOPs (which we may refer to as pNOP, for potential NOP) begins immediately downstream of a stop triplet in the reference human genome sequence, contains then at least ten amino acid-encoding triplets, and finishes with a stop.

Thus each gene as defined in the reference genome sequence includes a set of pNOPs. These NOPs are commonly not expressed in the human body, and if they were they would therefore be seen by the immune system as entirely foreign. Since, other than SNV-neoantigens, they are not a small change in a known peptide chain, but a longer stretch of foreign amino acid sequence, it is a priori to be expected that these NOPs are seen by the immune system on average as much more foreign and antigenic than SNV-neoantigens.

In the present invention simple insertions and deletions in coding regions are preferred, which—in order to cause a frame shift-could be of any length, but should not have a length that is 3 nucleotides or a multiple of 3 nucleotides, and should not create a novel stop triplet on the spot. Again, the set of such frame shift causing mutations is, like the set of SNV-causing mutations, virtually infinite: at every position in the 1.5% coding region of the genome almost any insertion or deletion (or net result from insertion plus deletion) of net change of sequence of + or − 1, 2, 4, 5, 7, 8 etc. nucleotides could bring a NOP in frame.

According to the invention provided are peptide based vaccines, meaning vaccines comprising the at least two neo out-of-frame peptides selected from SEQ ID Nos 1-4307, or nucleic acid based vaccines comprising a nucleic acid encoding at least two amino acid sequences selected from SEQ ID Nos 1-4307, to be used as personalized cancer vaccines.

A tumor of a patient can be screened for the presence of frame shift mutations, and once found a vaccine comprising the peptide which comprises among others the corresponding NOP can be used to immunize the patient, so the immune system of the patient will target the tumor cells expressing the neo antigen.

Thus, in some embodiments according to the invention, the peptide according to the invention is prepared/comprises at least two, preferably all the NOPs selected from SEQ ID 1-4307 and that have been identified in a cancer patient by screening for the presence of frame shift mutations that caused the NOP, or part thereof, to be encoded in the genome of the cancer cells of that patient. For example, if based on screening of tumor material from the patient, frame-shift mutations are identified in the patient and that encode for amino acid sequence with, for example, SEQ ID NO 1, SEQ ID NO 31, SEQ ID NO 231, and SEQ ID NO 756, the peptide according to the invention comprises at least two, e.g. SEQ ID NO 31 and SEQ ID NO 231, preferably all of these amino acid sequences. Alternatively an isolated nucleic acid may be provided, and that encodes for such peptide. According to this aspect of the invention, a vaccine can be provided that, in one vaccine, e.g. in one peptide or nucleic acid encoding such peptide, comprises all NOPs encoded or expressed in the cancer cells in that patient.

One issue that may arise when considering NOPs as personalized cancer vaccines is that once a tumor from a patient has been sequenced and one (or more) frame shift mutations have been identified, the corresponding NOP (or NOPs) need to be selected from the list of potential NOPS and made in a vaccine. This may be a time consuming process, while time is something the cancer patient usually lacks as the disease progresses. An "off-the-shelf" solution, where each NOP is already available as a vaccine may become available in the future, but it would be beneficial to provide for alternative approaches as well.

According to the invention, it has now surprisingly been found that an "off-the-shelf" (personalized) cancer vaccine can be achieved due to the finding that frame shift mutations in a relatively small number of genes contribute to a large extend to the presence of the total amount frame shift mutations identified in the TCGA patient cohort. This has led to the finding that, by combining multiple NOPs in a single peptide according to the invention (also referred to as polyNOP), with a library of relatively few peptides according to the invention used as vaccines a large percentage of the patients would be covered with a potential vaccine.

Figure 6:
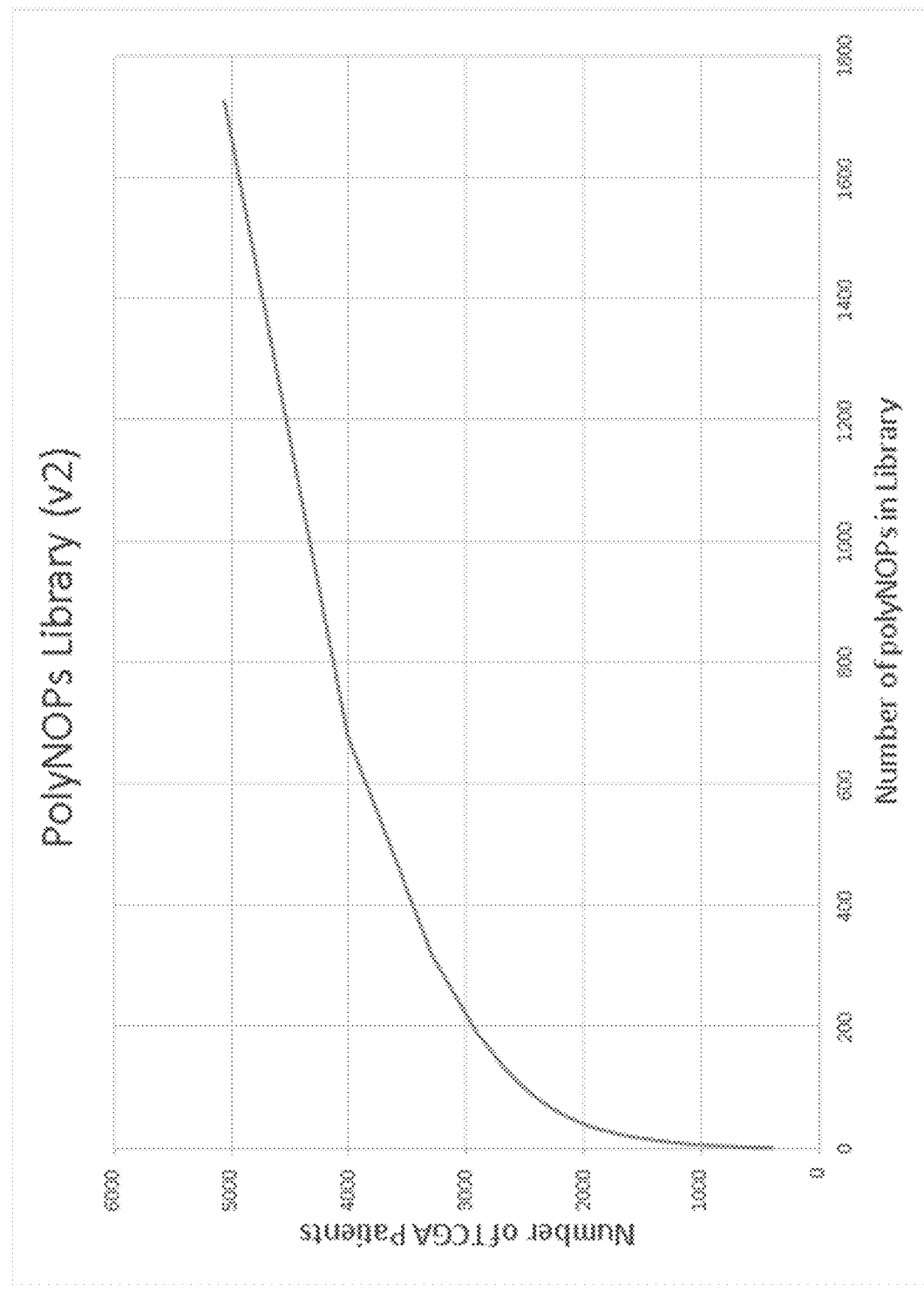
FIG. 6: Graphical representation of the number of patients in the TGCA cohort (https://cancergenome.nih.gov/publications/publicationguidelines) which have a frame shift mutation which is represented by a NOP (SEQ ID 1-4307) present in a library of polyNOP peptides, versus the amount of polyNOP peptides in present in the library. The data presented relates to the situation wherein each (individual) polyNOP covers all candidate NOPs for a single gene (e.g. all sequences of Group 1 or Group 2 or Group 3 . . . . Group 1103), and the polyNOPs are added to the library in order of abundance of frame shift mutations identified in said gene in the TCGA cohort, most frequent identified genes added first.

Table 1 was constructed by the inventor by identifying all genes for which frame shift mutation have been found in at least two separate patients in the TCGA patient cohort, and then sorting this list of genes from most frequently mutated (by frame shifts) to least frequently. Then for each identified frame shift mutation NOPs are identified that overlap with the frame shift mutations identified in the patients for each gene, and all these candidate NOPs are linked together to create a polyNOP for each gene. FIG. 6 presents a graphical representation of the number of patients in the TGCA cohort which have a frame shift mutation which is represented by a NOP (SEQ ID 1-4307) present in a library of polyNOP peptides, versus the amount of polyNOP peptides in present in the library. Using polyNOPs according to the invention for the 6 most frequently frame shifted genes (in tumors of cancer patients in the TCGA cohort), e.g. groups 1-6 in Table 1, the genes TP53 (SEQ ID Nos 1-21), ARID1A (SEQ ID Nos 22-61), KMT2D (SEQ ID Nos 62-100), GATA3 (SEQ ID Nos 101-109), APC (SEQ ID Nos 110-128) and PTEN (SEQ ID Nos 129-143), 10% of the patients in the TCGA would be covered, meaning a vaccine can be created for 10% of cancer patients from a polyNOP library of only 6 polyNOPs. By further extending this library to polyNOPs covering the 200 most frame shifted genes, about 30% of the patient's in the TCGA cohort would be covered.

In a preferred embodiment of the invention the vaccine comprises a peptide (or nucleic acid encoding this peptide) comprising all the candidate NOPs for a single gene, meaning each of the sequences of a group selected form the groups in Table 1. This makes it possible to construct a single vaccine for this gene which would be suitable for any patient which has a frame shift mutation in this gene, regardless of the location or reading frame.

The 1103 most frequently frame shifted genes identified by the above method are listed below in Table 1 together with the SEQ ID Nos representing the NOP peptides which overlap with the frame shift mutations identified in the patients.

TABLE 1

| Group No.: | Gene: | SEQ ID Nos: |
|---|---|---|
| 1 | TP53 | 1-21 |
| 2 | ARID1A | 22-61 |
| 3 | KMT2D | 62-100 |
| 4 | GATA3 | 101-109 |
| 5 | APC | 110-128 |
| 6 | PTEN | 129-143 |
| 7 | ZNF429 | 144-148 |
| 8 | VHL | 149-157 |
| 9 | CIC | 158-175 |
| 10 | ATRX | 176-193 |
| 11 | CDKN2A | 194-199 |
| 12 | PBRM1 | 200-223 |
| 13 | NF1 | 224-244 |
| 14 | RB1 | 245-254 |
| 15 | ZFP36L2 | 255-258 |
| 16 | ZFHX3 | 259-273 |

TABLE 1-continued

| Group No.: | Gene: | SEQ ID Nos: |
|---|---|---|
| 17 | CDH1 | 274-283 |
| 18 | ZFP36L1 | 284-295 |
| 19 | TTN | 296-327 |
| 20 | MAP3K1 | 328-340 |
| 21 | NOTCH1 | 341-354 |
| 22 | BAP1 | 355-364 |
| 23 | RUNX1 | 365-371 |
| 24 | KDM6A | 372-387 |
| 25 | SOX9 | 388-394 |
| 26 | KMT2C | 395-408 |
| 27 | MUC16 | 409-437 |
| 28 | ELF3 | 438-444 |
| 29 | PCLO | 445-461 |
| 30 | TOP2A | 462-468 |
| 31 | STK11 | 469-473 |
| 32 | FOXA1 | 474-479 |
| 33 | PCDHB2 | 480-484 |
| 34 | ARHGAP35 | 485-494 |
| 35 | FAT1 | 495-507 |
| 36 | ZNF750 | 508-512 |
| 37 | PIK3R1 | 513-519 |
| 38 | FLG | 520-556 |
| 39 | KMT2B | 557-571 |
| 40 | ARID2 | 572-580 |
| 41 | ZNF14 | 581-582 |
| 42 | FBN2 | 583-592 |
| 43 | BCOR | 593-600 |
| 44 | CDKN1A | 601-605 |
| 45 | HLA-A | 606-614 |
| 46 | ZNF814 | 615-618 |
| 47 | ARID5B | 619-623 |
| 48 | FBXW7 | 624-630 |
| 49 | CDK12 | 631-639 |
| 50 | AJUBA | 640-644 |
| 51 | TBX3 | 645-652 |
| 52 | CDKN1B | 653-656 |
| 53 | H2AFX | 657-658 |
| 54 | ZNF468 | 659-661 |
| 55 | MBD6 | 662-670 |

TABLE 1-continued

| Group No.: | Gene: | SEQ ID Nos: |
|---|---|---|
| 56 | SETD2 | 671-681 |
| 57 | MUC6 | 682-691 |
| 58 | MUC5B | 692-724 |
| 59 | BRCA2 | 725-734 |
| 60 | TCF12 | 735-744 |
| 61 | APOB | 745-752 |
| 62 | ROBO1 | 753-759 |
| 63 | LRP1B | 760-769 |
| 64 | CREBBP | 770-777 |
| 65 | NCOR2 | 778-789 |
| 66 | RNF43 | 790-798 |
| 67 | ZNF420 | 799-805 |
| 68 | HMCN1 | 806-813 |
| 69 | TLE1 | 814-818 |
| 70 | HOXA3 | 819-824 |
| 71 | AXIN1 | 825-830 |
| 72 | B2M | 831-833 |
| 73 | ASXL1 | 834-836 |
| 74 | NCOR1 | 837-840 |
| 75 | ALB | 841-845 |
| 76 | CSMD2 | 846-850 |
| 77 | ZNF675 | 851-853 |
| 78 | SRCAP | 854-864 |
| 79 | FUBP1 | 865-870 |
| 80 | ARID1B | 871-878 |
| 81 | FAT2 | 879-888 |
| 82 | LRP1 | 889-895 |
| 83 | ABCA13 | 896-904 |
| 84 | TGIF1 | 905-913 |
| 85 | DDX3X | 914-919 |
| 86 | SMAD4 | 920-922 |
| 87 | FOSL2 | 923-924 |
| 88 | HRNR | 925-945 |
| 89 | RANBP2 | 946-957 |
| 90 | JARID2 | 958-967 |
| 91 | YLPM1 | 968-972 |
| 92 | MGA | 973-982 |
| 93 | SPEN | 983-990 |
| 94 | TG | 991-999 |

TABLE 1-continued

| Group No.: | Gene: | SEQ ID Nos: |
|---|---|---|
| 95 | ITGA10 | 1000-1003 |
| 96 | ZMYM3 | 1004-1009 |
| 97 | ACVR2A | 1010-1015 |
| 98 | ZNF658 | 1016-1019 |
| 99 | COL11A1 | 1020-1026 |
| 100 | REV3L | 1027-1034 |
| 101 | CTNND2 | 1035-1040 |
| 102 | PLXNB2 | 1041-1046 |
| 103 | RBM15B | 1047-1050 |
| 104 | KRT5 | 1051-1053 |
| 105 | SELPLG | 1054-1055 |
| 106 | ZNF256 | 1056-1057 |
| 107 | ANKRD11 | 1058-1063 |
| 108 | COL18A1 | 1064-1074 |
| 109 | IRS1 | 1075-1080 |
| 110 | AHNAK2 | 1081-1138 |
| 111 | BCORL1 | 1139-1145 |
| 112 | COL7A1 | 1146-1154 |
| 113 | ZNF534 | 1155-1157 |
| 114 | ADAMTSL1 | 1158-1162 |
| 115 | ROCK2 | 1163-1167 |
| 116 | COL22A1 | 1168-1173 |
| 117 | INVS | 1174-1177 |
| 118 | MUC4 1 | 178-1188 |
| 119 | TNFAIP3 | 1189-1194 |
| 120 | KANSL1 | 1195-1200 |
| 121 | MYO10 | 1201-1204 |
| 122 | SEC63 | 1205-1205 |
| 123 | INPPL1 | 1206-1210 |
| 124 | KMT2A | 1211-1214 |
| 125 | TUBB4A | 1215-1217 |
| 126 | ASXL2 | 1218-1220 |
| 127 | GPS2 | 1221-1223 |
| 128 | OTOF | 1224-1227 |
| 129 | KDM5C | 1228-1231 |
| 130 | PRKARIA | 1232-1233 |
| 131 | ZNF613 | 1234-1235 |
| 132 | KEAP1 | 1236-1238 |
| 133 | ZFHX4 | 1239-1251 |
| 134 | ELMSAN1 | 1252-1258 |
| 135 | BCL9 | 1259-1265 |
| 136 | CACNA1A | 1266-1275 |
| 137 | DNAH5 | 1276-1285 |
| 138 | CUX1 | 1286-1291 |
| 139 | CAMSAP2 | 1292-1296 |
| 140 | NEB | 1297-1310 |
| 141 | RERE | 1311-1317 |
| 142 | TSHZ3 | 1318-1324 |
| 143 | DAZAP1 | 1325-1331 |
| 144 | EP300 | 1332-1337 |
| 145 | GAS2L2 | 1338-1341 |
| 146 | MEN1 | 1342-1345 |
| 147 | PCDHA6 | 1346-1347 |
| 148 | GSE1 | 1348-1352 |
| 149 | HIVEP3 | 1353-1360 |
| 150 | EPHA2 | 1361-1363 |
| 151 | SETD1B | 1364-1369 |
| 152 | KCND2 | 1370-1372 |
| 153 | KMT2E | 1373-1377 |
| 154 | LRRIQ1 | 1378-1381 |
| 155 | PRRC2A | 1382-1385 |
| 156 | RASA1 | 1386-1391 |
| 157 | RBM15 | 1392-1394 |
| 158 | COL11A2 | 1395-1404 |
| 159 | ITPR2 | 1405-1409 |
| 160 | TCF4 | 1410-1413 |
| 161 | TSC1 | 1414-1417 |
| 162 | MYO9B | 1418-1423 |
| 163 | PRKAB1 | 1424-1427 |
| 164 | CTAGE1 | 1428-1428 |
| 165 | PCDHGA11 | 1429-1431 |
| 166 | BCHE | 1432-1434 |
| 167 | CHST2 | 1435-1437 |
| 168 | KAT6B | 1438-1439 |
| 169 | PEG3 | 1440-1444 |
| 170 | FLNC | 1445-1448 |
| 171 | SPTBN2 | 1449-1452 |
| 172 | ALS2 | 1453-1456 |

TABLE 1-continued

| Group No.: | Gene: | SEQ ID Nos: |
|---|---|---|
| 173 | FAH | 1457-1457 |
| 174 | NF2 | 1458-1460 |
| 175 | PTPRC | 1461-1463 |
| 176 | RBM10 | 1464-1468 |
| 177 | TGFBR2 | 1469-1471 |
| 178 | ZNF436 | 1472-1473 |
| 179 | INHBA | 1474-1476 |
| 180 | PLCG1 | 1477-1479 |
| 181 | ADAMTS6 | 1480-1481 |
| 182 | GRIN3A | 1482-1483 |
| 183 | KIF1A | 1484-1485 |
| 184 | ASAH1 | 1486-1487 |
| 185 | BCL2L11 | 1488-1488 |
| 186 | FXR2 | 1489-1490 |
| 187 | RPL5 | 1491-1492 |
| 188 | SALL1 | 1493-1494 |
| 189 | ZFP64 | 1495-1497 |
| 190 | ZNF841 | 1498-1501 |
| 191 | ZNF90 | 1502-1507 |
| 192 | ANK3 | 1508-1515 |
| 193 | ATM | 1516-1524 |
| 194 | TNRC18 | 1525-1531 |
| 195 | ZNF607 | 1532-1533 |
| 196 | KIAA1217 | 1534-1548 |
| 197 | CTCF | 1549-1556 |
| 198 | POTEF | 1557-1561 |
| 199 | TRIOBP | 1562-1569 |
| 200 | ZNF292 | 1570-1577 |
| 201 | CUBN | 1578-1584 |
| 202 | FBN3 | 1585-1590 |
| 203 | KIAA1211 | 1591-1595 |
| 204 | FOXP4 | 1596-1604 |
| 205 | TNS2 | 1605-1607 |
| 206 | IGSF9B | 1608-1614 |
| 207 | PDZD2 | 1615-1619 |
| 208 | UNC79 | 1620-1623 |
| 209 | ZNF549 | 1624-1625 |
| 210 | HNRNPL | 1626-1627 |
| 211 | ARHGAP33 | 1628-1634 |
| 212 | ATP13A3 | 1635-1639 |
| 213 | LMTK3 | 1640-1642 |
| 214 | MEGF8 | 1643-1647 |
| 215 | PRRT2 | 1648-1651 |
| 216 | CHD3 | 1652-1658 |
| 217 | FLNA | 1659-1665 |
| 218 | HECA | 1666-1669 |
| 219 | ATXN2L | 1670-1682 |
| 220 | PCDHGA2 | 1683-1686 |
| 221 | KIAA2026 | 1687-1690 |
| 222 | TRPA1 | 1691-1693 |
| 223 | HMGB1 | 1694-1695 |
| 224 | HOXB3 | 1696-1698 |
| 225 | SZT2 | 1699-1703 |
| 226 | VWF | 1704-1709 |
| 227 | NKX2-2 | 1710-1712 |
| 228 | PRRC2B | 1713-1717 |
| 229 | TAF1C | 1718-1724 |
| 230 | TP53BP1 | 1725-1728 |
| 231 | ZDBF2 | 1729-1732 |
| 232 | CELSR3 | 1733-1737 |
| 233 | MED13 | 1738-1742 |
| 234 | NCOA6 | 1743-1748 |
| 235 | PHF20L1 | 1749-1752 |
| 236 | REPIN1 | 1753-1756 |
| 237 | TECTA | 1757-1761 |
| 238 | TNIK | 1762-1766 |
| 239 | ZNF687 | 1767-1771 |
| 240 | ACVR1B | 1772-1777 |
| 241 | CYP2B6 | 1778-1779 |
| 242 | DLX6 | 1780-1781 |
| 243 | FOXP1 | 1782-1787 |
| 244 | HDGF | 1788-1792 |
| 245 | NBPF10 | 1793-1793 |
| 246 | SCAF4 | 1794-1797 |
| 247 | SMAP1 | 1798-1800 |
| 248 | ADGRB1 | 1801-1802 |
| 249 | ASIC2 | 1803-1806 |
| 250 | MXD3 | 1807-1809 |

TABLE 1-continued

| Group No.: | Gene: | SEQ ID Nos: |
|---|---|---|
| 251 | NBPF9 | 1810-1812 |
| 252 | BRD2 | 1813-1817 |
| 253 | HOXD8 | 1818-1820 |
| 254 | KCNA6 | 1821-1823 |
| 255 | TBC1D10A | 1824-1826 |
| 256 | AARS2 | 1827-1829 |
| 257 | ATP1A2 | 1830-1832 |
| 258 | BCL3 | 1833-1834 |
| 259 | EWSR1 | 1835-1840 |
| 260 | IHH | 1841-1842 |
| 261 | KHSRP | 1843-1846 |
| 262 | MYOF | 1847-1850 |
| 263 | NLGN4X | 1851-1853 |
| 264 | PKHD1 | 1854-1856 |
| 265 | PLEKHA7 | 1857-1860 |
| 266 | RIPK4 | 1861-1864 |
| 267 | SF11 | 1865-1869 |
| 268 | SLC16A10 | 1870-1872 |
| 269 | SUN1 | 1873-1879 |
| 270 | VPS13B | 1880-1882 |
| 271 | ADAMTS5 | 1883-1885 |
| 272 | AFF4 | 1886-1888 |
| 273 | ATF7IP | 1889-1894 |
| 274 | CPEB4 | 1895-1896 |
| 275 | ING5 | 1897-1901 |
| 276 | MAPKBP1 | 1902-1903 |
| 277 | PLXNC1 | 1904-1906 |
| 278 | PTPRZ1 | 1907-1909 |
| 279 | ADAMTS15 | 1910-1912 |
| 280 | APBB1IP | 1913-1915 |
| 281 | BRD7 | 1916-1919 |
| 282 | CA1 | 1920-1920 |
| 283 | DOCK3 | 1921-1923 |
| 284 | GRIN2C | 1924-1925 |
| 285 | IRF7 | 1926-1928 |
| 286 | LRRN2 | 1929-1931 |
| 287 | NEIL1 | 1932-1936 |
| 288 | SLIT2 | 1937-1939 |
| 289 | TRAM1L1 | 1940-1941 |
| 290 | CBLN1 | 1942-1943 |
| 291 | DCLK1 | 1944-1945 |
| 292 | EED | 1946-1947 |
| 293 | GIGYF2 | 1948-1949 |
| 294 | MUC1 | 1950-1950 |
| 295 | NALCN | 1951-1952 |
| 296 | RAD21 | 1953-1954 |
| 297 | ADAL | 1955-1957 |
| 298 | AGL | 1958-1959 |
| 299 | DDIT4 | 1960-1961 |
| 300 | EHD3 | 1962-1963 |
| 301 | FZD5 | 1964-1964 |
| 302 | HES1 | 1965-1966 |
| 303 | LATS1 | 1967-1969 |
| 304 | MYB | 1970-1971 |
| 305 | NSRP1 | 1972-1973 |
| 306 | PLXND1 | 1974-1975 |
| 307 | POM121 | 1976-1977 |
| 308 | SEZ6L | 1978-1979 |
| 309 | SOX10 | 1980-1980 |
| 310 | SPTBN5 | 1981-1982 |
| 311 | ZNF408 | 1983-1984 |
| 312 | ETS2 | 1985-1985 |
| 313 | PCDH17 | 1986-1986 |
| 314 | VCL | 1987-1987 |
| 315 | WT1 | 1988-1988 |
| 316 | WWC3 | 1989-1989 |
| 317 | ZNF208 | 1990-2005 |
| 318 | ZNF43 | 2006-2014 |
| 319 | MAML2 | 2015-2016 |
| 320 | ZNF816 | 2017-2018 |
| 321 | FMN2 | 2019-2024 |
| 322 | ZNF714 | 2025-2026 |
| 323 | BCL9L | 2027-2034 |
| 324 | ZNF469 | 2035-2042 |
| 325 | ALG10 | 2043-2047 |
| 326 | CD93 | 2048-2051 |
| 327 | STAB1 | 2052-2058 |
| 328 | IRF2BPL | 2059-2060 |

TABLE 1-continued

| Group No.: | Gene: | SEQ ID Nos: |
|---|---|---|
| 329 | KDM6B | 2061-2068 |
| 330 | ZNF439 | 2069-2070 |
| 331 | PPIG | 2071-2075 |
| 332 | TET1 | 2076-2081 |
| 333 | DIDO1 | 2082-2086 |
| 334 | RBBP6 | 2087-2093 |
| 335 | SACS | 2094-2100 |
| 336 | KDM2B | 2101-2106 |
| 337 | MPRIP | 2107-2110 |
| 338 | PDS5B | 2111-2114 |
| 339 | BAHCC1 | 2115-2121 |
| 340 | FIGN | 2122-2125 |
| 341 | SLC9A4 | 2126-2129 |
| 342 | ADAMTS2 | 2130-2134 |
| 343 | ROCK1 | 2135-2140 |
| 344 | ZNF776 | 2141-2143 |
| 345 | PSD3 | 2144-2147 |
| 346 | NOS1 | 2148-2152 |
| 347 | ZNF233 | 2153-2153 |
| 348 | ARHGAP17 | 2154-2159 |
| 349 | ASPM | 2160-2167 |
| 350 | FAM214B | 2168-2170 |
| 351 | MAP1A | 2171-2175 |
| 352 | SMARCC2 | 2176-2184 |
| 353 | ARHGEF15 | 2185-2188 |
| 354 | DST | 2189-2192 |
| 355 | HECTD2 | 2193-2194 |
| 356 | HLA-B | 2195-2199 |
| 357 | MYOCD | 2200-2203 |
| 358 | TIE1 | 2204-2207 |
| 359 | WDFY3 | 2208-2211 |
| 360 | ALPK3 | 2212-2214 |
| 361 | DYRK1A | 2215-2217 |
| 362 | HGFAC | 2218-2222 |
| 363 | ITGB4 | 2223-2226 |
| 364 | TET3 | 2227-2230 |
| 365 | TNRC6B | 2231-2234 |
| 366 | ZNF443 | 2235-2237 |
| 367 | ZNF831 | 2238-2241 |
| 368 | AFF2 | 2242-2248 |
| 369 | COL4A1 | 2249-2253 |
| 370 | CTAGE9 | 2254-2256 |
| 371 | EPHB6 | 2257-2260 |
| 372 | GPR158 | 2261-2266 |
| 373 | LAMB1 | 2267-2270 |
| 374 | NOD2 | 2271-2273 |
| 375 | PRDM2 | 2274-2278 |
| 376 | RNF213 | 2279-2283 |
| 377 | TCF7 | 2284-2288 |
| 378 | TDRD5 | 2289-2291 |
| 379 | TRIM46 | 2292-2294 |
| 380 | COL8A1 | 2295-2299 |
| 381 | DMBT1 | 2300-2314 |
| 382 | FOLH1 | 2315-2318 |
| 383 | MIA3 | 2319-2323 |
| 384 | NAB2 | 2324-2327 |
| 385 | PRDM15 | 2328-2333 |
| 386 | TMEM92 | 2334-2335 |
| 387 | WASF3 | 2336-2339 |
| 388 | ZNF395 | 2340-2342 |
| 389 | AGO2 | 2343-2344 |
| 390 | BAG4 | 2345-2346 |
| 391 | COL6A3 | 2347-2352 |
| 392 | EGFLAM | 2353-2356 |
| 393 | EXPH5 | 2357-2360 |
| 394 | HOXA1 | 2361-2364 |
| 395 | INTU | 2365-2366 |
| 396 | MAP3K4 | 2367-2368 |
| 397 | MTA1 | 2369-2370 |
| 398 | MYRF | 2371-2374 |
| 399 | NRIP1 | 2375-2377 |
| 400 | NYAP1 | 2378-2379 |
| 401 | PLXNB1 | 2380-2382 |
| 402 | RTTN | 2383-2385 |
| 403 | SLC27A3 | 2386-2389 |
| 404 | TCF7L2 | 2390-2400 |
| 405 | TMEM184A | 2401-2402 |
| 406 | TOPBP1 | 2403-2404 |

TABLE 1-continued

| Group No.: | Gene: | SEQ ID Nos: |
|---|---|---|
| 407 | ACTN4 | 2405-2407 |
| 408 | COL9A2 | 2408-2411 |
| 409 | IGSF10 | 2412-2415 |
| 410 | JAG2 | 2416-2418 |
| 411 | KDM3B | 2419-2422 |
| 412 | KIAA0556 | 2423-2424 |
| 413 | KLHDC8B | 2425-2427 |
| 414 | MAP3K12 | 2428-2430 |
| 415 | NAV3 | 2431-2434 |
| 416 | NBEA | 2435-2439 |
| 417 | NFAT5 | 2440-2443 |
| 418 | NHLRC2 | 2444-2445 |
| 419 | NHS | 2446-2448 |
| 420 | PKHD1L1 | 2449-2451 |
| 421 | SLC4A2 | 2452-2456 |
| 422 | ADAM28 | 2457-2459 |
| 423 | AKAP9 | 2460-2463 |
| 424 | ARL13B | 2464-2467 |
| 425 | ATP1A1 | 2468-2471 |
| 426 | CAMTA1 | 2472-2474 |
| 427 | GPSM3 | 2475-2476 |
| 428 | HIVEP2 | 2477-2480 |
| 429 | ROS1 | 2481-2484 |
| 430 | SIPA1L2 | 2485-2488 |
| 431 | SLC6A6 | 2489-2490 |
| 432 | SYNE1 | 2491-2494 |
| 433 | TM9SF3 | 2495-2496 |
| 434 | TPR | 2497-2498 |
| 435 | TRIP10 | 2499-2501 |
| 436 | ZNF696 | 2502-2502 |
| 437 | DNMT3A | 2503-2505 |
| 438 | EGR3 | 2506-2507 |
| 439 | ELAC2 | 2508-2511 |
| 440 | ERICH3 | 2512-2515 |
| 441 | FAM98A | 2516-2518 |
| 442 | FBXO38 | 2519-2520 |
| 443 | FOXD4 | 2521-2522 |
| 444 | HSPG2 | 2523-2524 |
| 445 | MNDA | 2525-2526 |
| 446 | MTDH | 2527-2528 |
| 447 | MYH15 | 2529-2531 |
| 448 | NLRP7 | 2532-2535 |
| 449 | NOTCH2 | 2536-2539 |
| 450 | PTPRN | 2540-2544 |
| 451 | SRRM2 | 2545-2548 |
| 452 | TRAF3IP2 | 2549-2551 |
| 453 | AHNAK | 2552-2561 |
| 454 | ANK1 | 2562-2564 |
| 455 | ARHGEF10 | 2565-2570 |
| 456 | BCLAF1 | 2571-2572 |
| 457 | CCDC181 | 2573-2575 |
| 458 | CNOT4 | 2576-2578 |
| 459 | CP | 2579-2580 |
| 460 | DBF4 | 2581-2582 |
| 461 | DISP2 | 2583-2585 |
| 462 | F13A1 | 2586-2588 |
| 463 | FANCB | 2589-2590 |
| 464 | FCGBP | 2591-2595 |
| 465 | GRIK3 | 2596-2598 |
| 466 | NAA25 | 2599-2601 |
| 467 | NFATC2 | 2602-2604 |
| 468 | PTPN14 | 2605-2607 |
| 469 | PTPRB | 2608-2610 |
| 470 | ST6GALNAC3 | 2611-2614 |
| 471 | STAT6 | 2615-2617 |
| 472 | ZNF644 | 2618-2619 |
| 473 | ADGRG1 | 2620-2621 |
| 474 | ANKFY1 | 2622-2623 |
| 475 | BRAP | 2624-2624 |
| 476 | CDX2 | 2625-2626 |
| 477 | CNTLN | 2627-2628 |
| 478 | DOPEY2 | 2629-2630 |
| 479 | GNAZ | 2631-2632 |
| 480 | HDX | 2633-2634 |
| 481 | ITPKB | 2635-2636 |
| 482 | MYOM3 | 2637-2638 |
| 483 | NCAM2 | 2639-2643 |
| 484 | NCKAP5 | 2644-2645 |

TABLE 1-continued

| Group No.: | Gene: | SEQ ID Nos: |
|---|---|---|
| 485 | PCSK5 | 2646-2648 |
| 486 | PLXNA3 | 2649-2650 |
| 487 | RBMX2 | 2651-2652 |
| 488 | RTN1 | 2653-2655 |
| 489 | SCN2A | 2656-2658 |
| 490 | SEZ6L2 | 2659-2661 |
| 491 | SH3D21 | 2662-2664 |
| 492 | SIGLEC10 | 2665-2668 |
| 493 | SLC35G2 | 2669-2670 |
| 494 | SPDEF | 2671-2674 |
| 495 | SRSF11 | 2675-2676 |
| 496 | TAF3 | 2677-2678 |
| 497 | TET2 | 2679-2681 |
| 498 | TP53BP2 | 2682-2684 |
| 499 | UBC | 2685-2694 |
| 500 | ZC3H11A | 2695-2697 |
| 501 | ZFX | 2698-2699 |
| 502 | ACTB | 2700-2701 |
| 503 | AOC2 | 2702-2703 |
| 504 | ARMCX3 | 2704-2705 |
| 505 | ASTN2 | 2706-2707 |
| 506 | CD44 | 2708-2715 |
| 507 | CHEK2 | 2716-2717 |
| 508 | COX10 | 2718-2719 |
| 509 | CUL7 | 2720-2721 |
| 510 | CYP4F2 | 2722-2722 |
| 511 | ENKUR | 2723-2725 |
| 512 | FLCN | 2726-2726 |
| 513 | FOXO4 | 2727-2728 |
| 514 | HDAC4 | 2729-2730 |
| 515 | JUN | 2731-2732 |
| 516 | KCNJ3 | 2733-2734 |
| 517 | MED12 | 2735-2735 |
| 518 | NAA15 | 2736-2737 |
| 519 | P2RY11 | 2738-2739 |
| 520 | PGR | 2740-2741 |
| 521 | PHB | 2742-2743 |
| 522 | PNPLA3 | 2744-2745 |
| 523 | RBM14 | 2746-2747 |
| 524 | RBMX | 2748-2749 |
| 525 | RHBDF1 | 2750-2751 |
| 526 | SCAP | 2752-2753 |
| 527 | SMC4 | 2754-2755 |
| 528 | STK31 | 2756-2757 |
| 529 | SUPT20H | 2758-2760 |
| 530 | TM6SF2 | 2761-2762 |
| 531 | ZNF518B | 2763-2764 |
| 532 | ZNF615 | 2765-2766 |
| 533 | ZNF804A | 2767-2767 |
| 534 | ARID4B | 2768-2769 |
| 535 | BAZ2B | 2770-2771 |
| 536 | C9orf152 | 2772-2772 |
| 537 | CARD6 | 2773-2774 |
| 538 | CBFB | 2775-2775 |
| 539 | CNTNAP1 | 2776-2777 |
| 540 | COG5 | 2778-2779 |
| 541 | COL14A1 | 2780-2781 |
| 542 | CPT1B | 2782-2783 |
| 543 | DBF4B | 2784-2785 |
| 544 | DDX5 | 2786-2786 |
| 545 | DEPDC5 | 2787-2788 |
| 546 | DPY19L2 | 2789-2790 |
| 547 | E2F3 | 2791-2793 |
| 548 | EDNRB | 2794-2795 |
| 549 | EPAS1 | 2796-2797 |
| 550 | FBP1 | 2798-2799 |
| 551 | FBXO15 | 2800-2801 |
| 552 | GOT1 | 2802-2803 |
| 553 | GRAP2 | 2804-2804 |
| 554 | HIST1H1C | 2805-2806 |
| 555 | HNRNPA1 | 2807-2808 |
| 556 | HTR2B | 2809-2810 |
| 557 | HTR3A | 2811-2812 |
| 558 | IGSF1 | 2813-2814 |
| 559 | KCNN2 | 2815-2816 |
| 560 | KHDRBS1 | 2817-2818 |
| 561 | KIF5B | 2819-2820 |
| 562 | MRPS22 | 2821-2821 |

TABLE 1-continued

| Group No.: | Gene: | SEQ ID Nos: |
|---|---|---|
| 563 | MTRR | 2822-2823 |
| 564 | MTUS1 | 2824-2825 |
| 565 | PCDHGA8 | 2826-2827 |
| 566 | PDZRN3 | 2828-2829 |
| 567 | POLM | 2830-2833 |
| 568 | PRDM16 | 2834-2835 |
| 569 | RASSF1 | 2836-2839 |
| 570 | RLIM | 2840-2841 |
| 571 | SYNJ1 | 2842-2844 |
| 572 | TAP2 | 2845-2847 |
| 573 | TFCP2 | 2848-2849 |
| 574 | TMEM100 | 2850-2850 |
| 575 | TRIM15 | 2851-2852 |
| 576 | TRMT112 | 2853-2853 |
| 577 | TROAP | 2854-2856 |
| 578 | UNG | 2857-2858 |
| 579 | VN1R1 | 2859-2859 |
| 580 | ZNF445 | 2860-2861 |
| 581 | ARIH2 | 2862-2863 |
| 582 | COL21A1 | 2864-2864 |
| 583 | DBR1 | 2865-2865 |
| 584 | DESI2 | 2866-2866 |
| 585 | FRMD3 | 2867-2867 |
| 586 | HSPD1 | 2868-2868 |
| 587 | KLK12 | 2869-2872 |
| 588 | MAGEA3 | 2873-2873 |
| 589 | MTBP | 2874-2874 |
| 590 | NCDN | 2875-2875 |
| 591 | P2RY8 | 2876-2876 |
| 592 | PDE4A | 2877-2877 |
| 593 | RBM48 | 2878-2878 |
| 594 | REM2 | 2879-2879 |
| 595 | RSPH1 | 2880-2881 |
| 596 | SEC22A | 2882-2882 |
| 597 | SLC23A1 | 2883-2884 |
| 598 | SPRY2 | 2885-2885 |
| 599 | STK39 | 2886-2886 |
| 600 | TCEAL5 | 2887-2887 |
| 601 | TPBG | 2888-2888 |
| 602 | WAC | 2889-2890 |
| 603 | ACER2 | 2891-2891 |
| 604 | AFTPH | 2892-2892 |
| 605 | AGTR1 | 2893-2893 |
| 606 | ALPP | 2894-2894 |
| 607 | ARFGAP2 | 2895-2896 |
| 608 | ARVCF | 2897-2897 |
| 609 | ATP10B | 2898-2898 |
| 610 | ATP13A1 | 2899-2899 |
| 611 | AURKAIP1 | 2900-2900 |
| 612 | BASP1 | 2901-2901 |
| 613 | BTBD10 | 2902-2902 |
| 614 | CBR1 | 2903-2903 |
| 615 | CD274 | 2904-2904 |
| 616 | CEP68 | 2905-2905 |
| 617 | CYP2R1 | 2906-2906 |
| 618 | DET1 | 2907-2907 |
| 619 | DOCK6 | 2908-2908 |
| 620 | DUSP16 | 2909-2909 |
| 621 | EME1 | 2910-2910 |
| 622 | EP400 | 2911-2911 |
| 623 | ESYT1 | 2912-2912 |
| 624 | FAM227B | 2913-2913 |
| 625 | FBXO45 | 2914-2914 |
| 626 | FTO | 2915-2915 |
| 627 | GOLGA3 | 2916-2916 |
| 628 | GPRC5A | 2917-2917 |
| 629 | HAS3 | 2918-2918 |
| 630 | HHIPL 1 | 2919-2919 |
| 631 | HIPK2 | 2920-2920 |
| 632 | HIST1H4J | 2921-2921 |
| 633 | HMGCL | 2922-2922 |
| 634 | HSPA8 | 2923-2924 |
| 635 | IKZF4 | 2925-2925 |
| 636 | IL1RL1 | 2926-2926 |
| 637 | ISCA1 | 2927-2927 |
| 638 | KCNQ5 | 2928-2928 |
| 639 | KCNT2 | 2929-2929 |
| 640 | KIFC3 | 2930-2930 |

TABLE 1-continued

| Group No.: | Gene: | SEQ ID Nos: |
|---|---|---|
| 641 | KLF15 | 2931-2931 |
| 642 | KLF6 | 2932-2932 |
| 643 | KLHL28 | 2933-2933 |
| 644 | LRRC14 | 2934-2934 |
| 645 | LYST | 2935-2935 |
| 646 | MRPL22 | 2936-2936 |
| 647 | NFAM1 | 2937-2937 |
| 648 | NFIX | 2938-2939 |
| 649 | NONO | 2940-2940 |
| 650 | NPM1 | 2941-2941 |
| 651 | POGZ | 2942-2942 |
| 652 | PTGER4 | 2943-2943 |
| 653 | RGMB | 2944-2944 |
| 654 | RHEBL1 | 2945-2945 |
| 655 | RREB1 | 2946-2946 |
| 656 | RTN3 | 2947-2947 |
| 657 | SLC25A43 | 2948-2948 |
| 658 | SMCR8 | 2949-2949 |
| 659 | SNAI3 | 2950-2950 |
| 660 | SOS1 | 2951-2951 |
| 661 | STEAP4 | 2952-2953 |
| 662 | SYN1 | 2954-2954 |
| 663 | TCFL5 | 2955-2955 |
| 664 | TFAP2A | 2956-2956 |
| 665 | TINF2 | 2957-2957 |
| 666 | TMED1 | 2958-2958 |
| 667 | TMEM120A | 2959-2959 |
| 668 | TOB2 | 2960-2960 |
| 669 | TOM1 | 2961-2962 |
| 670 | TRMT61B | 2963-2963 |
| 671 | TTC16 | 2964-2964 |
| 672 | TUBA1A | 2965-2966 |
| 673 | UBXN1 | 2967-2968 |
| 674 | USH1C | 2969-2969 |
| 675 | UTP3 | 2970-2970 |
| 676 | ZBED2 | 2971-2971 |
| 677 | ZNF628 | 2972-2973 |
| 678 | ZNF141 | 2974-2977 |
| 679 | ZNF761 | 2978-2981 |
| 680 | ZFP3 | 2982-2982 |
| 681 | PTCH1 | 2983-2992 |
| 682 | BTBD7 | 2993-3002 |
| 683 | RAI1 | 3003-3007 |
| 684 | FAM193A | 3008-3012 |
| 685 | ZC3H18 | 3013-3016 |
| 686 | ZNF529 | 3017-3019 |
| 687 | PCDHB4 | 3020-3023 |
| 688 | SYNE2 | 3024-3034 |
| 689 | AXIN2 | 3035-3042 |
| 690 | ITGAX | 3043-3045 |
| 691 | SCN9A | 3046-3052 |
| 692 | C5orf42 | 3053-3059 |
| 693 | JAK1 | 3060-3064 |
| 694 | MECOM | 3065-3069 |
| 695 | MKL1 | 3070-3073 |
| 696 | PNISR | 3074-3079 |
| 697 | POLG | 3080-3081 |
| 698 | TTF1 | 3082-3083 |
| 699 | ANKRD12 | 3084-3086 |
| 700 | CPAMD8 | 3087-3090 |
| 701 | FOXA2 | 3091-3094 |
| 702 | HECTD4 | 3095-3100 |
| 703 | IRX3 | 3101-3104 |
| 704 | PEAR1 | 3105-3108 |
| 705 | ZMYM1 | 3109-3112 |
| 706 | ADNP | 3113-3118 |
| 707 | CASP8 | 3119-3124 |
| 708 | GAS6 | 3125-3127 |
| 709 | HDLBP | 3128-3134 |
| 710 | OBSCN | 3135-3146 |
| 711 | PYGO2 | 3147-3148 |
| 712 | RBM27 | 3149-3150 |
| 713 | SBF1 | 3151-3154 |
| 714 | ZBTB41 | 3155-3157 |
| 715 | ABR | 3158-3163 |
| 716 | BRF1 | 3164-3168 |
| 717 | FOXQ1 | 3169-3171 |
| 718 | GTF3C1 | 3172-3180 |

TABLE 1-continued

| Group No.: | Gene: | SEQ ID Nos: |
|---|---|---|
| 719 | HSPB8 | 3181-3182 |
| 720 | KIAA0100 | 3183-3187 |
| 721 | NAV1 | 3188-3194 |
| 722 | RYR1 | 3195-3200 |
| 723 | SPRED1 | 3201-3203 |
| 724 | TSPYL2 | 3204-3205 |
| 725 | ZNF677 | 3206-3207 |
| 726 | ATP10D | 3208-3211 |
| 727 | DLGAP3 | 3212-3214 |
| 728 | ERG | 3215-3219 |
| 729 | KCNH4 | 3220-3223 |
| 730 | ULK2 | 3224-3226 |
| 731 | COL4A2 | 3227-3231 |
| 732 | DYSF | 3232-3236 |
| 733 | FHDC1 | 3237-3239 |
| 734 | GDF5 | 3240-3242 |
| 735 | MDN1 | 3243-3246 |
| 736 | NOTCH3 | 3247-3250 |
| 737 | PCDHB13 | 3251-3253 |
| 738 | PCDHB14 | 3254-3256 |
| 739 | PCDHB3 | 3257-3259 |
| 740 | POLR2A | 3260-3263 |
| 741 | PPP6R2 | 3264-3267 |
| 742 | RAE1 | 3268-3270 |
| 743 | RP1L1 | 3271-3278 |
| 744 | TACC2 | 3279-3283 |
| 745 | WRN | 3284-3287 |
| 746 | ARMCX5-GPRASP2 | 3288-3292 |
| 747 | ATN1 | 3293-3296 |
| 748 | C1orf112 | 3297-3298 |
| 749 | CHD1 | 3299-3302 |
| 750 | CLGN | 3303-3306 |
| 751 | DNAH6 | 3307-3310 |
| 752 | KNOP1 | 3311-3314 |
| 753 | LTBP4 | 3315-3317 |
| 754 | MAML3 | 3318-3318 |
| 755 | MED23 | 3319-3322 |
| 756 | MSH3 | 3323-3326 |
| 757 | RING1 | 3327-3329 |
| 758 | SETBP1 | 3330-3334 |
| 759 | UBR5 | 3335-3337 |
| 760 | ZNF484 | 3338-3340 |
| 761 | ZNF541 | 3341-3344 |
| 762 | ZNF627 | 3345-3346 |
| 763 | ABCB1 | 3347-3349 |
| 764 | AKAP12 | 3350-3353 |
| 765 | BSN | 3354-3359 |
| 766 | BTRC | 3360-3361 |
| 767 | CHD8 | 3362-3366 |
| 768 | COPA | 3367-3369 |
| 769 | DENND4B | 3370-3371 |
| 770 | DNAH10 | 3372-3376 |
| 771 | KIDINS220 | 3377-3380 |
| 772 | MARK2 | 3381-3390 |
| 773 | MTSS1 | 3391-3395 |
| 774 | NBEAL1 | 3396-3398 |
| 775 | NYNRIN | 3399-3403 |
| 776 | OAS2 | 3404-3406 |
| 777 | PHF21A | 3407-3410 |
| 778 | PRPF40A | 3411-3414 |
| 779 | PRTG | 3415-3416 |
| 780 | ROBO2 | 3417-3421 |
| 781 | RPRD2 | 3422-3423 |
| 782 | SCAF1 | 3424-3426 |
| 783 | TCOF1 | 3427-3431 |
| 784 | XRCC2 | 3432-3433 |
| 785 | ZNF177 | 3434-3436 |
| 786 | ZNF790 | 3437-3438 |
| 787 | ADGRA2 | 3439-3441 |
| 788 | CASD1 | 3442-3445 |
| 789 | EPHA4 | 3446-3448 |
| 790 | FAS | 3449-3450 |
| 791 | FOXN2 | 3451-3454 |
| 792 | FXR1 | 3455-3457 |
| 793 | HNF1A | 3458-3459 |
| 794 | LARP1 | 3460-3463 |
| 795 | MAP3K11 | 3464-3466 |
| 796 | MKI67 | 3467-3468 |

TABLE 1-continued

| Group No.: | Gene: | SEQ ID Nos: |
|---|---|---|
| 797 | NSD1 | 3469-3473 |
| 798 | PTCH2 | 3474-3476 |
| 799 | SHANK2 | 3477-3481 |
| 800 | UBR4 | 3482-3483 |
| 801 | XRN1 | 3484-3485 |
| 802 | ZNF670 | 3486-3486 |
| 803 | ZNF780A | 3487-3490 |
| 804 | ALCAM | 3491-3492 |
| 805 | ASAP2 | 3493-3495 |
| 806 | CLUH | 3496-3498 |
| 807 | FIGNL1 | 3499-3500 |
| 808 | GRIK2 | 3501-3504 |
| 809 | HDAC2 | 3505-3507 |
| 810 | HELZ2 | 3508-3510 |
| 811 | HERC2 | 3511-3514 |
| 812 | IL7R | 3515-3515 |
| 813 | JAG1 | 3516-3519 |
| 814 | PDZD4 | 3520-3526 |
| 815 | PLOD3 | 3527-3528 |
| 816 | PSD2 | 3529-3531 |
| 817 | RASA2 | 3532-3533 |
| 818 | RFC1 | 3534-3537 |
| 819 | RNF217 | 3538-3540 |
| 820 | SLITRK2 | 3541-3544 |
| 821 | ST6GALNAC5 | 3545-3548 |
| 822 | SYCP2 | 3549-3551 |
| 823 | TRIP12 | 3552-3553 |
| 824 | UGT1A9 | 3554-3555 |
| 825 | AHDC1 | 3556-3559 |
| 826 | C21orf59-TCP10L | 3560-3561 |
| 827 | CBX8 | 3562-3562 |
| 828 | COL1A2 | 3563-3565 |
| 829 | DSCAML1 | 3566-3569 |
| 830 | EHBP1 | 3570-3573 |
| 831 | FRAS1 | 3574-3577 |
| 832 | GIGYF1 | 3578-3579 |
| 833 | GRB14 | 3580-3581 |
| 834 | HSF4 | 3582-3584 |
| 835 | IFIH1 | 3585-3587 |
| 836 | JADE1 | 3588-3589 |
| 837 | KIF21A | 3590-3593 |
| 838 | LAMC3 | 3594-3595 |
| 839 | LOC107987545 | 3596-3596 |
| 840 | MED12L | 3597-3601 |
| 841 | MEX3B | 3602-3603 |
| 842 | MYO15A | 3604-3605 |
| 843 | PSMC4 | 3606-3608 |
| 844 | RBM33 | 3609-3612 |
| 845 | RBPJ | 3613-3615 |
| 846 | SCRIB | 3616-3616 |
| 847 | SEMA5B | 3617-3621 |
| 848 | SENP6 | 3622-3623 |
| 849 | TAF15 | 3624-3626 |
| 850 | TUBGCP6 | 3627-3631 |
| 851 | UGT1A1 | 3632-3632 |
| 852 | WDR44 | 3633-3635 |
| 853 | YBX2 | 3636-3636 |
| 854 | ZBED4 | 3637-3638 |
| 855 | ZHX2 | 3639-3642 |
| 856 | ZRANB2 | 3643-3644 |
| 857 | AHCTF1 | 3645-3647 |
| 858 | BRD1 | 3648-3652 |
| 859 | C19orf47 | 3653-3654 |
| 860 | CCAR1 | 3655-3657 |
| 861 | CCDC120 | 3658-3661 |
| 862 | CERK | 3662-3663 |
| 863 | COBLL1 | 3664-3665 |
| 864 | COL16A1 | 3666-3667 |
| 865 | COL17A1 | 3668-3670 |
| 866 | DCLK3 | 3671-3671 |
| 867 | DDR1 | 3672-3675 |
| 868 | DNAJC1 | 3676-3678 |
| 869 | DROSHA | 3679-3682 |
| 870 | EGR1 | 3683-3684 |
| 871 | ENTPD2 | 3685-3685 |
| 872 | ETV1 | 3686-3690 |
| 873 | FILIP1L | 3691-3692 |
| 874 | GBE1 | 3693-3694 |

TABLE 1-continued

| Group No.: | Gene: | SEQ ID Nos: |
|---|---|---|
| 875 | GGNBP2 | 3695-3696 |
| 876 | HP1BP3 | 3697-3698 |
| 877 | IGF2R | 3699-3700 |
| 878 | ITSN1 | 3701-3705 |
| 879 | KIAA0391 | 3706-3708 |
| 880 | LAMP3 | 3709-3710 |
| 881 | LILRB5 | 3711-3714 |
| 882 | LTBR | 3715-3718 |
| 883 | MAP1B | 3719-3722 |
| 884 | MAST2 | 3723-3725 |
| 885 | MICALL2 | 3726-3727 |
| 886 | MRPS5 | 3728-3729 |
| 887 | NEK1 | 3730-3732 |
| 888 | NUP214 | 3733-3735 |
| 889 | PHLPP1 | 3736-3736 |
| 890 | PLEKHM1 | 3737-3737 |
| 891 | PRG4 | 3738-3740 |
| 892 | PSME4 | 3741-3743 |
| 893 | RAPH1 | 3744-3746 |
| 894 | RNF25 | 3747-3748 |
| 895 | RYR3 | 3749-3752 |
| 896 | SAP130 | 3753-3758 |
| 897 | SENP7 | 3759-3760 |
| 898 | SLC12A7 | 3761-3763 |
| 899 | SMARCA1 | 3764-3766 |
| 900 | SOCS3 | 3767-3768 |
| 901 | SPEF2 | 3769-3772 |
| 902 | TBCK | 3773-3774 |
| 903 | TJP2 | 3775-3779 |
| 904 | TNKS | 3780-3781 |
| 905 | TNRC6C | 3782-3784 |
| 906 | TNS3 | 3785-3788 |
| 907 | WDFY4 | 3789-3791 |
| 908 | ZBTB20 | 3792-3793 |
| 909 | ZC3H12B | 3794-3797 |
| 910 | ZNF212 | 3798-3798 |
| 911 | ZNF318 | 3799-3802 |
| 912 | ABCA5 | 3803-3805 |
| 913 | ADAMTSL2 | 3806-3808 |
| 914 | ALDOB | 3809-3811 |
| 915 | ATAD2 | 3812-3814 |
| 916 | BDP1 | 3815-3817 |
| 917 | BTAF1 | 3818-3819 |
| 918 | C1QA | 3820-3820 |
| 919 | CDHR2 | 3821-3822 |
| 920 | CENPF | 3823-3824 |
| 921 | CEP162 | 3825-3826 |
| 922 | CHD9 | 3827-3830 |
| 923 | CIR1 | 3831-3832 |
| 924 | CLCA4 | 3833-3834 |
| 925 | CLCN3 | 3835-3838 |
| 926 | CNTNAP3 | 3839-3840 |
| 927 | COL15A1 | 3841-3843 |
| 928 | CUL9 | 3844-3846 |
| 929 | DCX | 3847-3853 |
| 930 | EPB41L3 | 3854-3857 |
| 931 | EPN2 | 3858-3859 |
| 932 | FAM168B | 3860-3861 |
| 933 | FCHO2 | 3862-3863 |
| 934 | GLI1 | 3864-3865 |
| 935 | GLIS1 | 3866-3867 |
| 936 | GLYR1 | 3868-3871 |
| 937 | HEPACAM2 | 3872-3874 |
| 938 | HERC1 | 3875-3877 |
| 939 | HERC3 | 3878-3879 |
| 940 | HHIP | 3880-3882 |
| 941 | INF2 | 3883-3887 |
| 942 | KCNH2 | 3888-3889 |
| 943 | KIAA1324L | 3890-3891 |
| 944 | MED25 | 3892-3894 |
| 945 | MKRN3 | 3895-3896 |
| 946 | NCOA3 | 3897-3898 |
| 947 | OSM | 3899-3900 |
| 948 | PAPLN | 3901-3904 |
| 949 | PCDHB12 | 3905-3906 |
| 950 | PHGR1 | 3907-3907 |
| 951 | PPP2R5B | 3908-3910 |
| 952 | SEC24C | 3911-3913 |

TABLE 1-continued

| Group No.: | Gene: | SEQ ID Nos: |
|---|---|---|
| 953 | SMC3 | 3914-3915 |
| 954 | SMC6 | 3916-3918 |
| 955 | SPATA2L | 3919-3920 |
| 956 | SPG7 | 3921-3923 |
| 957 | STAU2 | 3924-3926 |
| 958 | STON1 | 3927-3929 |
| 959 | TNKS1BP1 | 3930-3933 |
| 960 | TNRC6A | 3934-3935 |
| 961 | ZBTB22 | 3936-3938 |
| 962 | ZKSCAN4 | 3939-3940 |
| 963 | ZNF609 | 3941-3943 |
| 964 | ADAMTS9 | 3944-3946 |
| 965 | ANKRD36 | 3947-3952 |
| 966 | ANXA11 | 3953-3955 |
| 967 | ARHGAP30 | 3956-3958 |
| 968 | ATL1 | 3959-3959 |
| 969 | BMP2K | 3960-3961 |
| 970 | C19orf44 | 3962-3963 |
| 971 | CASKIN2 | 3964-3965 |
| 972 | CDH13 | 3966-3968 |
| 973 | CIITA | 3969-3970 |
| 974 | CSF1 | 3971-3973 |
| 975 | ESPL1 | 3974-3976 |
| 976 | ESPNL | 3977-3978 |
| 977 | EYA1 | 3979-3983 |
| 978 | FRMD4A | 3984-3986 |
| 979 | GBP1 | 3987-3989 |
| 980 | GTPBP10 | 3990-3990 |
| 981 | HCFC2 | 3991-3993 |
| 982 | HOXD3 | 3994-3996 |
| 983 | IL21R | 3997-3999 |
| 984 | KAT5 | 4000-4003 |
| 985 | KDM5B | 4004-4005 |
| 986 | KIAA0825 | 4006-4007 |
| 987 | KLHL36 | 4008-4010 |
| 988 | LRP2 | 4011-4013 |
| 989 | LTN1 | 4014-4016 |
| 990 | MAGED1 | 4017-4019 |
| 991 | MED13L | 4020-4021 |
| 992 | MGAT5 | 4022-4022 |
| 993 | MMP10 | 4023-4024 |
| 994 | MMP12 | 4025-4026 |
| 995 | MRPL12 | 4027-4028 |
| 996 | MSLN | 4029-4030 |
| 997 | N4BP2 | 4031-4033 |
| 998 | NAALADL1 | 4034-4036 |
| 999 | NCAM1 | 4037-4039 |
| 1000 | NRROS | 4040-4042 |
| 1001 | PCDHGB4 | 4043-4045 |
| 1002 | PER1 | 4046-4048 |
| 1003 | PLEC | 4049-4059 |
| 1004 | PLEKHG2 | 4060-4063 |
| 1005 | RAB40C | 4064-4064 |
| 1006 | REXO1 | 4065-4066 |
| 1007 | RPS6KA4 | 4067-4068 |
| 1008 | SEC31A | 4069-4071 |
| 1009 | SH2B1 | 4072-4073 |
| 1010 | SH3D19 | 4074-4077 |
| 1011 | SIGLEC9 | 4078-4080 |
| 1012 | SLC16A12 | 4081-4081 |
| 1013 | SLC38A3 | 4082-4084 |
| 1014 | SMARCAD1 | 4085-4087 |
| 1015 | SNX18 | 4088-4089 |
| 1016 | SQLE | 4090-4090 |
| 1017 | SREK1 | 4091-4092 |
| 1018 | SUPT5H | 4093-4094 |
| 1019 | SYDE1 | 4095-4098 |
| 1020 | TBC1D10C | 4099-4100 |
| 1021 | TEX1 4 | 4101-4103 |
| 1022 | TMEM161B | 4104-4106 |
| 1023 | TRIM41 | 4107-4109 |
| 1024 | USP40 | 4110-4111 |
| 1025 | ZNF432 | 4112-4113 |
| 1026 | ABCA12 | 4114-4116 |
| 1027 | ABCC9 | 4117-4119 |
| 1028 | ADAMTS18 | 4120-4121 |
| 1029 | AKAP6 | 4122-4123 |
| 1030 | ASAP1 | 4124-4125 |

TABLE 1-continued

| Group No.: | Gene: | SEQ ID Nos: |
|---|---|---|
| 1031 | BAHD1 | 4126-4127 |
| 1032 | CCDC148 | 4128-4128 |
| 1033 | CCDC30 | 4129-4130 |
| 1034 | CD22 | 4131-4133 |
| 1035 | CDK13 | 4134-4136 |
| 1036 | CMYA5 | 4137-4137 |
| 1037 | COL6A6 | 4138-4140 |
| 1038 | CPVL | 4141-4141 |
| 1039 | CTNND1 | 4142-4145 |
| 1040 | DACT1 | 4146-4147 |
| 1041 | DCHS2 | 4148-4150 |
| 1042 | DHX15 | 4151-4153 |
| 1043 | DSP | 4154-4155 |
| 1044 | EPHA1 | 4156-4157 |
| 1045 | ERBB3 | 4158-4160 |
| 1046 | EVPL | 4161-4163 |
| 1047 | FAM160A2 | 4164-4165 |
| 1048 | FBXL19 | 4166-4167 |
| 1049 | FGGY | 4168-4168 |
| 1050 | FOXC2 | 4169-4169 |
| 1051 | GAS2L1 | 4170-4172 |
| 1052 | GPR37 | 4173-4174 |
| 1053 | HNRNPM | 4175-4176 |
| 1054 | HTATSF1 | 4177-4178 |
| 1055 | IARS2 | 4179-4181 |
| 1056 | IFI16 | 4182-4183 |
| 1057 | IFNAR1 | 4184-4185 |
| 1058 | IGSF8 | 4186-4188 |
| 1059 | IREB2 | 4189-4191 |
| 1060 | JAK3 | 4192-4192 |
| 1061 | KCNA3 | 4193-4194 |
| 1062 | LARP4B | 4195-4198 |
| 1063 | LENG9 | 4199-4200 |
| 1064 | LRRC8E | 4201-4204 |
| 1065 | MDM1 | 4205-4207 |
| 1066 | MNX1 | 4208-4208 |
| 1067 | NFATC4 | 4209-4214 |
| 1068 | NUMA1 | 4215-4217 |
| 1069 | PATZ1 | 4218-4219 |
| 1070 | PCNT | 4220-4222 |
| 1071 | PDLIM4 | 4223-4224 |
| 1072 | PHTF2 | 4225-4227 |
| 1073 | PLEKHA4 | 4228-4231 |
| 1074 | POR | 4232-4233 |
| 1075 | POSTN | 4234-4236 |
| 1076 | PRKCA | 4237-4239 |
| 1077 | PRPF40B | 4240-4242 |
| 1078 | PRUNE2 | 4243-4246 |
| 1079 | RALGAPA1 | 4247-4248 |
| 1080 | RBM12B | 4249-4250 |
| 1081 | SDK1 | 4251-4253 |
| 1082 | SHROOM2 | 4254-4255 |
| 1083 | SLC12A9 | 4256-4261 |
| 1084 | SLC4A5 | 4262-4262 |
| 1085 | SLC9B2 | 4263-4264 |
| 1086 | SLIT1 | 4265-4266 |
| 1087 | SPOCD1 | 4267-4269 |
| 1088 | SREBF2 | 4270-4271 |
| 1089 | TFDP2 | 4272-4273 |
| 1090 | TRIM27 | 4274-4276 |
| 1091 | TTLL4 | 4277-4279 |
| 1092 | UHRF1BP1 | 4280-4282 |
| 1093 | USP36 | 4283-4285 |
| 1094 | UTP14C | 4286-4288 |
| 1095 | VARS | 4289-4290 |
| 1096 | WDR81 | 4291-4292 |
| 1097 | ZDHHC8 | 4293-4295 |
| 1098 | ZKSCAN1 | 4296-4297 |
| 1099 | ZNF155 | 4298-4298 |
| 1100 | ZNF337 | 4299-4300 |
| 1101 | ZNF48 | 4301-4302 |
| 1102 | ZNF507 | 4303-4305 |
| 1103 | ZNF672 | 4306-4307 |

It is to be noted that the tumors in the TCGA are of different people, with different disease (one will be a Caucasian with a glioblastoma, the other of Japanese descent with a colon cancer) but they have one thing in common: they have cancer. That means that with the funneling effect described above a vaccine for many different tumors in different people can be provided by combining multiple NOPs in a single peptide according to the invention.

In summary, the present invention is based on the surprising finding that despite the fact that there are infinite possibilities for frame shift mutations in the human genome, a vaccine can be developed that targets a frame shift mutation in a tumor with potential use in a large population of cancer patients. This can be done by combining multiple NOPs in a single peptide. Doing so would allow for "off-the-shelf" personalized vaccines.

Peptides according to the invention comprising of polyNOPs or nucleic acids encoding such, when used as a vaccine, provide the following advantages:

a vaccine constructed from a single polyNOP, as opposed to single NOP, can benefit a large number of patients. For example, a polyNOP comprising multiple NOPs for a single gene as listed in Table 1, wherein the polyNOP comprises for example two or more or each sequence listed for the gene in Table 1, makes the polyNOP suitable for many more patients having a frame shift mutation in the gene. In case each sequence as listed in Table 1 for a gene is included the polyNOP would cover all frame shift mutations for that gene as identified in the TCGA patient cohort. Therefore such a polyNOP (comprising each sequence listed in Table 1 for a single gene (group)), would cover any frame shift mutation for said gene, as opposed to vaccines based on single NOPs, in which case for each frame shift mutation the corresponding NOP needs to be elected, which could be the same NOP but more likely is not. This makes it feasible to construct and/or test the polyNOP in advance and have the vaccine available off-the-shelf. This greatly reduces the time from screening a tumor from a patient to administering a potential vaccine for said tumor to the patient, as it eliminates the time of production, testing and approval. For example, the tumor of a cancer patient is sequenced and reveals a frame shift mutation in a certain gene. The polyNOP vaccine according to this invention and for this respective gene can now be administered to the patient, because the vaccine was already constructed and tested it is available immediately. For example, in case the patients comprises a frame shift mutation in gene KMT2D (group 3 in Table 1) causing the expressing of a NOP, it can be provided with a vaccine according to the invention that is based on two or more, preferably all of SEQ ID Nos 62-100, representing the NOPs for said gene. The same vaccine is available for a further patient that also comprises a frame shift mutation in KMT2D causing the expression of a NOP, even if the mutation is different from the mutation of the first patient, for example the mutation is at another location in the same gene or is an indel that is larger or smaller, or is an indel of same size, but causing a codon for a different amino acid.

a vaccine library of polyNOP based vaccines can be constructed for the most frequently frame shifted genes (in tumors). The added advantage of such library is that in case multiple frame shift mutations are identified in a tumor from a patient, a combination of polyNOP based vaccines can be administered, thereby increasing the likelihood that an immune response is raised against the tumor. An additional advantage is that with a library of limited size a relatively large percentage of patients can be covered with a potential vaccine.

Generally speaking and in one embodiment, the workflow for providing an antigenic peptide for use in an immunogenic composition is as follows. When a patient is diagnosed with a cancer for example a biopsy may be taken from the tumor, or a sample set is taken of the tumor after resection. The genome, exome or transcriptome is sequenced by existing methods. The outcome is compared, for example using a web interface or software, to the polyNOP library. This will identify and display hits. In turn a patient and/or physician can, if they desire, be informed whether or not hits have been found. On average this is expected for up to 30% of the cases.

In its broadest sense there is provided for a peptide comprising at least two amino acid sequences, wherein each of said amino acid sequence is independently selected from the group consisting of SEQ ID Nos 1 to 4307. Sequences 1-4307 in the sequence listing each represent potential NOPs which have also been identified in the tumors of cancer patients in the TCGA cohort, meaning they are the longest possible NOPs that correspond with the NOPs which are expressed due to a frame shift in these patients.

By combining multiple amino acid sequences selected from the group consisting of SEQ ID Nos 1 to 4307, in one and the same peptide, the amount of potential patients that could be treated is increased. Therefore it is disclosed herein that any at least two amino acid sequences may be selected from the group consisting of SEQ ID Nos 1 to 4307 in order to increase the amount of potential patients that may be treated according to the current invention. For example, from the group consisting of SEQ ID Nos 1 to 4307, those amino acid amino acid sequences may be selected to correspond to those genomic regions that are most frequently hit by a frameshift mutation causing the expression of the NOPs are discussed herein. According to the invention it is however preferred to select for each peptide amino acid sequences belonging to the same gene (meaning sequences selected from the same group as listed in Table 1), or alternatively create a combination of the amino acid sequences selected from SEQ ID Nos 1-4307 covering the area's most frequently hit by frame shift mutations.

Combining at least two sequences would increase the potential pool of patients that could be treated by a peptide according to the invention, however it may be beneficial to construct the peptide according to the invention with more sequences selected from the group consisting of SEQ ID Nos 1 to 4307, for example using 3, 4, 5, 6, 7, 8, 9, 10, or more sequences.

The term "independently selected" should be interpreted as that the at least two sequences selected are not the same sequence.

The skilled person is aware that naturally variations may occur in the genome resulting in variation in proteins encoded by the human exome. It is therefore considered that a amino acid sequence may have at least 90% sequence homology with a sequence selected from the group consisting of SEQ ID Nos 1 to 4307, preferably 91%, 92%, 93%, 94%, 95%, 96%, 97%, 98% or 99%, most preferably 100% sequence homology. Likewise, preferably the full length sequences as listed are used in the construction of the peptide according to the invention, however for practical considerations it may be possible to truncate the sequences for various reasons for example in order to prevent redundancy (i.e. to prevent the presence of more than one stretch of amino acids with (near) identical amino acid sequence, and wherein such stretch comprises at least 5, 6, 7, 8 or more amino acids). Therefore it is also disclosed herein that in some embodiments, the peptide according to the invention can be constructed with amino acid sequences each independently having 80%, 81%, 82%, 83%, 84%, 85%, 86%, 87%, 88%, 98%, 90%, 91%, 92%, 93%, 94%, 95%, 96%, 97%, 98% or 99%, most preferably 100% of the length of sequences selected from the group consisting of SEQ ID Nos 1 to 4307.

It is to be noted that the amino acid sequences selected from the group consisting of SEQ ID Nos 1 to 4307 may be included in the peptide in any order, therefore the order is not limited to, for example, the order in which the different amino acid sequences appear in Table 1, or the order in which the corresponding NOPs appear in a protein. For example, in case the peptide according to the invention would comprise two or more of the SEQ ID Nos 973-982 (Group 92 in Table 1, the MGA gene), for example, would comprise SEQ ID NO 973, 977 and 982, these amino acid sequences may be present in the peptide according to the invention, for example, in the order 973-977-982, but also, for example, 977-973-982 or 982-973-977 or any other order, In some preferred embodiments each of said amino acid sequences in the peptide according to the invention is independently selected from the sequences of one group selected from the groups 1 to 1103 as listed in Table 1.

Figure 3:
FIG. 3: Graphical representation of the selection of candidate NOPs for a single identified frame shift mutation in a tumor of a cancer patient. The top bar represents a normal protein sequence, below that is a representation of the protein encoded in the tumor, where the frame shift mutation results in a neo open reading frame (in grey) until a stop codon is encountered. Below that are all potential NOP sequences for this protein, meaning all amino acid sequences that can be expressed in the +1 and −1 reading frames. Overlapping NOPs are selected by taking those NOPs which have corresponding nucleotide sequences with the area surrounding the frame shift location but in a different reading frame, as indicated with the dashed line (in this case NOP 3 for the +1 reading frame and NOP 7 for the −1 reading frame). Overlapping NOPs are then combined to form a single peptide, the individual NOP sequences are either directly linked or linked through an amino acid linker sequence.
Figure 3:
Figure 3:
Figure 3:

Table 1 lists NOPs which overlap with frame shift mutations identified in tumors of cancer patients, and represent a set of the most frequent encountered frame shift mutations. For example FIG. 3 provides a visual example of a protein, and a protein containing a NOP resulting from a frame shift in a patient. Below are visualized all the potential NOPs that could be encoded by the +1 and -1 reading frame. The NOPs indicated with the dashed line are said to overlap, they are the longest possible NOPs that either include the NOP sequence found in the patient or include an amino acid sequence encoded by the alternative reading frame. For example the NOP found in the patient is in the +1 reading frame, the longest potential NOP that contains the same sequence is NOP 3, the corresponding NOP in the alternative reading frame (-1) is NOP 7, as it is encoded by the same nucleotide sequence but in the alternative reading frame (chosen from the frame shifted reading frames +1 and -1).

The list in Table 1 is sorted per gene (groups) and then sorted from genes in which most frequently a frame shift mutation is identified to less frequent. The sequence mentioned per group (e.g. SEQ ID NO 110-128 for group 5 (the gene APC) are NOPs identified for said gene. According to the invention, in a preferred embodiment, it is beneficial to construct the peptide according to the invention based on amino acid sequences from table 1 and derived from the same gene (i.e. from one group as identified in Table 1, for example and preferably 2, 3, 4, 5, 6, 7, 8, 9, or 10 or more sequences from the same group and representing a single gene.

It is however not excluded that amino acid sequences from other genes (i.e. groups in Table 1) are still included in the peptide according to the invention, and/or in case a gene (group in Table 1) is only represented by a few amino acid sequences. It may be combined with amino acid sequences of another gene, for example, because it is also represented by only a few sequences.

In some preferred embodiment the number of amino acid sequences selected from the one group selected from the groups 1 to 1103 are (X-Y) sequences, wherein X represents the total number of sequences in the selected group and Y represents an integer with a value ranging from 0 to (X-2).

The amount of sequences being (X-Y) sequences, wherein X represents the total number of sequences in the selected group and Y represents an integer with a value ranging from 0 to (X-2), selected from one group selected from the groups 1 to 1103 means that at least two sequences are selected from the same group (e.g Group 1 in Table 1), up to and including each of the sequences in said group *e.g. Group 1). For example if the group comprises 10 sequences, 2, 3, 4, 5, 6, 7, 8, 9, or 10 sequences may be selected.

In a preferred embodiment the peptide comprises all of the amino acid sequences listed in Table 1 for the selected group. For example in case group 1 is selected (gene TP53) the peptide comprises each of the sequences with SEQ ID Nos 1-21.

In some preferred embodiment said amino acid sequences comprised in the peptide according to the invention are directly adjacent to each other in the peptide, and/or between said amino acid sequences a linker amino acid sequence may be present. Preferably n between each of said amino acid sequences in the peptide according to the invention linker amino acid sequence is present. Preferably wherein said linker amino acid sequences, independently, have a length of 1, 2, 3, 4 or 5, or more amino acids.

It is disclosed herein that in the peptide according to the invention the amino acid sequences (e.g. those selected from SEQ ID NO 1-4307) may either be directly linked to each other or that they may be linked through linker amino acid sequences.

The use of linker amino acid sequences may be beneficial for example for introducing, among others, signal peptides or cleavage sites. Therefore each connection of the amino acid sequences (e.g. those selected from SEQ ID NO. 1-4307) in the peptide according to the invention may independently be either a direct link of the amino acid sequences (i.e. no linker amino acid sequence, no additional amino acids are present) or an indirect link through a linker amino acid sequence.

In some preferred embodiment at least one, preferably all of the linker amino acid sequences have the amino acid sequence VDD.

Also provided for is an isolated nucleic acid comprising a nucleotide sequence encoding the peptide according to the invention.

It is disclosed herein that both peptide and nucleotide based vaccines are suitable to achieve the effect of the invention. The skilled person will be capable of constructing a nucleic acid with a nucleotide sequence encoding the peptide as described herein using standard codon usage. For example, the nucleic acid having the desired nucleotide sequence can be constructed de novo. As will be understood any other and different codon usage can be implemented.

TABLE 2 most frequently used codon for each amino acid and most frequently used stop codon.

| | |
|---|---|
| A | GCC |
| C | TGC |
| D | GAC |
| E | GAG |
| F | TTC |
| G | GGC |
| H | CAC |
| I | ATC |
| K | AAG |

TABLE 2-continued most frequently used codon for each amino acid and most frequently used stop codon.

| | |
|---|---|
| L | CTG |
| M | ATG |
| N | AAC |
| P | CCC |
| Q | CAG |
| R | CGG |
| S | AGC |
| T | ACC |
| V | GTG |
| W | TGG |
| Y | TAC |
| Stop | TGA |

In some preferred embodiment in said isolated nucleic acid at least 50%, 60%, 70%, 80%, 90%, or 100% of the amino acids in the peptide are encoded by a codon corresponding to a codon presented in Table 2.

Table 2 lists for each acid amino acid (and the stop codon) the most frequently used codon as encountered in the human exome.

It is found that there are several advantages to using the most frequently used codons as listed in Table 2.

First of all it increases the likelihood of the peptide being expressed well. Second, by using different codons, for example using the codons of Table 2, the nucleotide sequence of the nucleic acid according to the invention, and in particular those parts of the nucleic acid that encode for the amino acid sequences comprised in the peptide according to the invention are distinct from the nucleotide sequence as these will be found in the genome of the patient having a frameshift mutation that causes the expression of a NOP as described herein. In other words, the nucleic acid still includes nucleotide sequence that encodes for such NOP, but these nucleotide sequences are different from the corresponding nucleotide sequences as found in a particular patient. If in the nucleic acid according to the invention a further, and undesired, frameshift mutation occurs, this will never cause for the expression of the wild-type protein (or part thereof) because of the changed codon usage.

With at least 50%, 60%, 70%, 80%, 90%, or 100% of the amino acids in the peptide are encoded by a codon corresponding to a codon presented in Table 2 is meant that at least 50%, 60%, 70%, 80%, 90%, or 100% of the codons used in the peptide encoding nucleotide sequence are codons selected from Table 2.

In some preferred embodiment in said isolated nucleic acid, if a linker amino acid sequence is present in the peptide encoded by the nucleic acid, each nucleotide sequence in the nucleic acid that encodes a linker amino acid sequence individually comprises at least one codon triplet, wherein the at least one codon triplet is chosen such that it codes for a stop codon when in the nucleic acid a frame shift occurs upstream of said out of frame stop codon, preferably wherein said codon triplet is chosen from the group consisting of: ATA, CTA, GTA, TTA, ATG, CTG, GTG, TTG, AAA, AAC, AAG, AAT, AGA, AGC, AGG, AGT, GAA, GAC, GAG, and GAT. These codons do not code for a stop codon, but could create a stop codon in case of a frame shift, such as when read in the +1, +2, +4, +, 5, etc. reading frame. For example, two amino acid encoding sequences are linked by a linker amino acid encoding sequence as follows (linker amino acid encoding sequence in bold):

CTATACAGGCGAATGAGATTATG

Resulting in the following amino acid sequence (amino acid linker sequence in bold):

LYRRMRL

In case of a +1 frame shift, the following sequence is encoded:

YTGE[stop]DY

As can be seen, the amino acid linker encoding sequence results in a stop codon.

An additional advantage may be presented by including out of frame stop codons in the sequences encoding the linker amino acid sequences in the peptide. In case a frame shift occurs in the nucleotide sequence encoding the peptide such out of frame stop codon ensures that the reading frame is terminated.

In some preferred embodiments in said isolated nucleic acid the linker amino acid sequences are encoded by the nucleotide sequence GTAGATGAC.

In a most preferred embodiment, the linker amino acid sequences are encoded by the nucleotide sequence GTAGATGAC, as it harbors two out of frame stop codons (TAG and TGA), one in the +1 and one in the −1 reading frame. The amino acid sequence encoded by this nucleotide sequence is VDD. The added advantage of using a nucleotide sequence encoding for this linker amino acid sequence is that any frame shift will result in a stop codon, wherein frame shift is defined as a shift in the sequence resulting in a new open reading frame.

Also provided for is a vector comprising an isolated nucleic acid according to the invention.

Vectors, including plasmid vectors, eukaryotic viral vectors and expression vectors are known to the skilled person. Vectors may be used to express a recombinant gene construct in eukaryotic cells depending on the preference and judgment of the skilled practitioner (see, for example, Sambrook et al., Chapter 16). For example, many viral vectors are known in the art including, for example, retroviruses, adeno-associated viruses, and adenoviruses. Other viruses useful for introduction of a gene into a cell include, but a not limited to, herpes virus, mumps virus, poliovirus, Sindbis virus, and vaccinia virus, such as, canary pox virus. The methods for producing replication-deficient viral particles and for manipulating the viral genomes are well known.

Also provided for is an expression vector comprising a promoter operably linked to an isolated nucleic acid according to the invention.

The nucleotide sequences of the present invention can be contained in an expression vector. An "expression vector" is a DNA element, often of circular structure, having the ability to replicate autonomously in a desired host cell, or to integrate into a host cell genome and also possessing certain well-known features which, for example, permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art.

The expression vector can also be an RNA element that contains the sequences required to initiate translation in the desired reading frame, and possibly additional elements that are known to stabilize or contribute to replicate the RNA molecules after administration. Therefore when used herein the term DNA when referring to an isolated nucleic acid encoding the peptide according to the invention should be interpreted as referring to DNA from which the peptide can be transcribed or RNA molecules from which the peptide can be translated.

Also provided for is a host cell comprising an isolated nucleic acid according to the invention, or a vector according to the invention or an expression vector according to the invention.

The DNA or RNA construct of the present invention may be introduced into a cell (prokaryotic or eukaryotic) by standard methods. As used herein, the terms "transformation" and "transfection" are intended to refer to a variety of art recognized techniques to introduce a DNA into a host cell. Such methods include, for example, transfection, including, but not limited to, liposome-polybrene, DEAE dextran-mediated transfection, electroporation, calcium phosphate precipitation, microinjection, or velocity driven microprojectiles ("biolistics"). Such techniques are well known by one skilled in the art. See, Sambrook et al. (1989) Molecular Cloning: A Laboratory Manual (2 ed. Cold Spring Harbor Lab Press, Plainview, N.Y.). Alternatively, one could use a system that delivers the DNA construct in a gene delivery vehicle. The gene delivery vehicle may be viral or chemical. Various viral gene delivery vehicles can be used with the present invention. In general, viral vectors are composed of viral particles derived from naturally occurring viruses. The naturally occurring virus has been genetically modified to be replication defective and does not generate additional infectious viruses, or it may be a virus that is known to be attenuated and does not have unacceptable side effects.

Also provided for is a vaccine comprising the peptide according to the invention, or the isolated nucleic acid according to the invention, or the vector according to the invention, or the expression vector according to the invention, optionally further comprising a pharmaceutically acceptable excipient.

In some embodiments, the vaccine comprises a pharmaceutically acceptable excipient and/or an adjuvant. The compositions may contain pharmaceutically acceptable auxiliary substances as required to approximate physiological conditions, such as pH adjusting and buffering agents, tonicity adjusting agents, wetting agents and the like. Suitable adjuvants are well-known in the art and include but are not limited to, aluminum (or a salt thereof, e.g., aluminium phosphate and aluminium hydroxide), monophosphoryl lipid A, squalene (e.g., MF59), montanide, hiltonol, poly-ICLC (polyriboinosinic-polyribocytidylic acid-polylysine carboxymethylcellulose), liposomes (e.g. CAF09, cationic adjuvant formulation 09), Amplivant, Resiquimod, Iscomatrix and cytosine phosphoguanine (CpG). A skilled person is able to determine the appropriate adjuvant, if necessary, and an immune-effective amount thereof. As used herein, an immune-effective amount of adjuvant refers to the amount needed to increase the vaccine's immunogenicity in order to achieve the desired effect.

Also disclosed herein, the immunogenic composition or vaccine is capable of raising a specific T-cell response. The vaccine composition comprises either peptides or isolated nucleic acid as described herein. A person skilled in the art can, when desired, select preferred peptides or isolated nucleic acid by testing, for example, the generation of T-cells in vitro as well as their efficiency and overall presence, the proliferation, affinity and expansion of certain T-cells for certain peptides, and the functionality of the T-cells, e.g. by analyzing the IFN-γ production or tumor killing by T-cells. However this is not required, given that the peptides according to the invention are in their entirety foreign to the body and thus potentially highly antigenic.

Also provided for is the vaccine according to the invention for use in the prevention or treatment of a disease, preferably wherein said disease is cancer.

The vaccine according to the invention can be administered alone or in combination with other therapeutic agents. The therapeutic agent is for example, a chemotherapeutic agent, radiation, or immunotherapy. Any suitable therapeutic treatment r a particular, cancer may be administered. Examples of chemotherapeutic agents include, but are not limited to bleomycin, capecitabine, carboplatin, cisplatin, cyclophosphamide, docetaxel, doxorubicin, etoposide, interferon alpha, irinotecan, lansoprazole, levamisole, methotrexate, metoclopramide, mitomycin, omeprazole, ondansetron, paclitaxel, pilocarpine, rituxitnab, tamoxifen, taxol, trastuzumab, vinblastine, and vinorelbine tartrate.

The subject may, in some embodiments, be further administered an anti-immunosuppressive/immunostimulatory agent. For example, the subject is further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each peptide to be included in the vaccine composition and the optimum dosing regimen can be determined by one skilled in the art without undue experimentation. The composition may be prepared for injection of the peptide, DNA or RNA encoding the peptide, or any other carrier comprising such (such as a virus or liposomes). For example, doses of between 1 and 500 mg 50 µg and 1.5 mg, preferably 125 µg to 500 µg, of peptide or DNA may be given and will depend from the respective peptide or DNA. Other methods of administration of the immunogenic compositions are known to the skilled person.

The vaccine may be prepared so that the selection, number and/or amount of peptides present in the composition is patient-specific. Selection of one or more peptides is based on sequencing information from the tumor of the patient. For any frame shift mutation found a corresponding NOP is selected, in which case the polyNOP according to the invention is selected for the vaccine. In case multiple frame shift mutations are found, multiple polyNOPs with corresponding NOPs may be selected for the vaccine. For example, in the tumor of a patient two frame shift mutations were identified, in the genes PTEN and VHL. The polyNOPs comprising SEQ ID NOS 129-143 (PTEN) and the polyNOP comprising the SEQ ID Nos 149-157 (VHL) can be selected for this patient. The selection may also be dependent on the specific type of cancer, the status of the disease, earlier treatment regimens, the immune status of the patient, and, HLA-haplotype of the patient. Furthermore, the vaccine can contain individualized components, according to personal needs of the particular patient.

In therapeutic applications, vaccines are administered to a patient in an amount sufficient to elicit an effective CTL response to the tumor antigen and to cure or at least partially arrest symptoms and/or complications. An amount adequate to accomplish this is defined as "therapeutically effective dose."

For therapeutic use, administration should preferably begin at or shortly after the detection or surgical removal of tumors. This is followed by boosting doses until at least symptoms are substantially abated and for a period thereafter. For that reason being able to provide the immunogenic composition off-the-shelf or in a short period of time is very important. Preferably, the immunogenic compositions are administered parenterally, e.g., intravenously, subcutaneously, intradermally, intramuscularly, or otherwise. The compositions may contain pharmaceutically acceptable auxiliary substances as required to approximate physiological conditions, such as pH adjusting and buffering agents, tonicity adjusting agents, wetting agents and the like.

For therapeutic purposes, nucleic acids encoding a peptide and optionally one or more of the peptides described herein can also be administered to the patient. Thus a vaccine can comprise multiple isolated nucleic acids as described herein. For example a vaccine can comprise an isolated nucleic acid encoding the sequences of group 2 (gene is ARID1A, SEQ ID Nos 22-61), an isolated nucleic acid encoding the sequences of group 4 (gene is GATA3, SEQ ID Nos 101-109) and an isolated nucleic acid encoding the sequences of group 9 (gene is CIC, SEQ ID Nos 158-175). A number of methods are conveniently used to deliver the nucleic acids to the patient. For instance, the nucleic acid can be delivered directly, as "naked DNA". The peptides and polypeptides can also be expressed by attenuated viral hosts, such as vaccinia or fowlpox. This approach involves the use of vaccinia virus as a vector to express nucleotide sequences that encode the peptide. Upon introduction into the subject the recombinant vaccinia virus expresses the peptide according to the invention, and thereby elicits a host CTL response. Vaccinia vectors and methods useful in immunization protocols are described in, e.g., U.S. Pat. No. 4,722,848. Another vector is BCG (Bacille Calmette Guerin) as described in Stover et al. (Nature 351:456-460 (1991)).

Also provided for is a library comprising 2, 3, 4, 5, 6, 7, 8, 9, 10, 20, 30, or more vaccines according to the invention, each vaccine individually comprising at least two, preferably all, amino acid sequences selected from a group selected from the groups 1-1103 as listed in Table 1, or a nucleotide sequence encoding said amino acid sequences, and wherein said 2, 3, 4, 5, 6, 7, 8, 9, 10, 20, 30, or more vaccines each comprise amino acid sequences, or nucleotide sequences encoding said amino acid sequences, from a different group selected from the groups of sequences listed in Table 1. For example, a library may comprise a first vaccine comprising a peptide with 2 or more sequences selected from group 6 of Table 1 or an isolated nucleic acid encoding such peptide, a second vaccine comprising a peptide with 2 or more sequences selected from group 23 of Table 1 or an isolated nucleic acid encoding such peptide, and a third vaccine comprising a peptide with 2 or more sequences selected from group 78 of Table 1 or an isolated nucleic acid encoding such peptide.

A particular advantage is to construct a library of vaccines according to the invention, as it substantially increases the potential of a suitable vaccine being available for a patient wherein a frame shift mutation has been identified in the tumor DNA or RNA. For example, if vaccines are constructed comprising each sequence of one group of Table 1 (i.e. a first vaccine comprising a peptide comprising each of the SEQ ID Nos 1-21 of group 1, or the isolated nucleic acid encoding such peptide, a second vaccine comprising a peptide comprising each of the SEQ ID Nos 176-193 of group 10, or the isolated nucleic acid encoding such peptide), a third vaccine comprising a peptide comprising each of the SEQ ID Nos 245-254 of group 14, or the isolated nucleic acid encoding such peptide)), by constructing a library of these vaccines representing the first 6 groups, a potential vaccine is available for 10% of the patients represented by the TCGA patient cohort.

In some preferred embodiment said library of 2, 3, 4, 5, 6, 7, 8, 9, 10, 20, 30, or more vaccines comprises vaccines each individually comprising at least two, preferably all, amino acid sequences selected from a group selected from the groups 1 to 2, 1 to 3, 1 to 4, 1 to 5, 1 to 6, 1 to 7, 1 to 8, 1 to 9, 1 to 10, 1 to 20, 1 to 30, or 1 to more selected from the groups of sequences listed in Table 1, or nucleotide sequences encoding said amino acid sequences. For example, the library comprises a first vaccine comprising a peptide with two or more sequences form group 1, a second vaccine comprising a peptide with two or more sequences from group 2, a third vaccine with a peptide comprising two or more sequences from group 3 and a fourth vaccine comprising a peptide with two or more sequences from group 4.

When used herein groups 1 to 2 means 1 up to and including 2, groups 1 to 3 mean up to and including 3, etc. Furthermore "1 to more" is used to represent the option when "more" is chosen as the number of vaccine (meaning, more than 30, so for example 31), and is meant to represent the groups 1 up to and including the number representing the number of vaccines selected for the library. In a particularly preferred embodiment, the library comprises 200 vaccines according to the invention, said 200 vaccines comprises sequences selected from groups 1 to 200 selected from the groups of sequences listed in Table 1, or nucleotide sequences encoding said amino acid sequences. For example, the library comprises a vaccine 1 comprising a peptide with at least 2 preferably all of the sequences of group 1, and a vaccine 2 comprising a peptide with at least 2 preferably all of the sequences of group 2, and a vaccine 3 comprising a peptide with at least 2 preferably all of the sequences of group 3, and . . . , and a vaccine 200 comprising a peptide with at least 2 preferably all of the sequences of group 200.

Also provided for is a method for generating a nucleic acid coding for a peptide, the method comprising the steps of:

a) identifying frame shift mutations in the tumor DNA and/or RNA of a cohort of cancer patients in order to obtain a frame shift library;

b) identifying at least one gene which is changed by a frame shift mutation in the tumor DNA and/or RNA of one or more patients in the cohort of cancer patients to obtain a frame shift gene;

c) identifying each novel open reading frame in both the +1 and −1 reading frame that overlaps with or is adjacent to the frame shift location of the frame shifted gene to obtain candidate novel open reading frame sequences;

d) optionally when present, identifying each novel open reading frames in both the +1 and −1 reading frame that overlaps with or is adjacent to the frame shift location for each alternative splicing construct of the frame shift gene to obtain candidate novel alternative splicing open reading frame sequences;

e) combining each of the candidate open reading frame sequences and optionally the candidate novel alternative splicing open reading frame sequences of the frame shift gene in a nucleic acid construct.

Identification of frame shift mutations can be done by sequencing of RNA or DNA using methods known to the skilled person. Sequencing of the genome, exome or transcriptome may be complete, targeted or partial. In some embodiments the sequencing is complete (whole sequencing). In some embodiments the sequencing is targeted. With targeted sequencing is meant that purposively certain region or portion of the genome, exome or transcriptome are sequenced. For example targeted sequencing may be directed to only sequencing for sequences in the set of sequences obtained from the cancer patient that would provide for a match with one or more of the sequences in the sequence listing, for example by using specific primers. In some embodiment only portion of the genome, exome or transcriptome is sequenced. The skilled person is well-aware of methods that allow for whole, targeted or partial sequencing of the genome, exome or transcriptome of a tumor sample of a patient.

For example any suitable sequencing-by-synthesis platform can be used including the Genome Sequencers from Roche/454 Life Sciences, the 1G Analyzer from Illumina/Solexa, the SOLID system from Applied BioSystems, and the Heliscope system from Helicos Biosciences. The method of sequencing the genome, exome or transcriptome is not in particular limited within the context of the present invention.

In some preferred embodiments the genome is sequenced. In some preferred embodiments the exome is sequenced. In some preferred embodiments the transcriptome is sequenced. Preferably the transcriptome is sequenced, in particular the mRNA present in a sample from a tumor of the patient. The transcriptome is representative of genes and neo open reading frame peptides as defined herein being expressed in the tumor in the patient.

Following sequencing of the tumor, using any sequencing method known in the art, the tumor sequences are aligned and compared to a reference genome. Sequence comparison can be performed by any suitable means available to the skilled person. Indeed the skilled person is well equipped with methods to perform such comparison, for example using software tools like BLAST and the like, or specific software to align short or long sequence reads, accurate or noisy sequence reads to a reference genome, e.g. the human reference genome GRCh37 or GRCh38. A match is identified when a sequence identified in the patients material and a sequence as disclosed herein have a string, i.e. a peptide sequence (or RNA or DNA sequence encoding such peptide (sequence) in case the comparison is on the level of RNA or DNA) in common representative of at least 8, preferably at least 10 adjacent amino acids. Furthermore, sequence reads derived from a patients cancer genome (or transcriptome) can partially match the genomic DNA sequences encoding the amino acid sequences as disclosed herein, for example if such sequence reads are derived from exon/intron boundaries or exon/exon junctions, or if part of the sequence aligns upstream (to the 5' end of the gene) of the position of a frameshift mutation. Analysis of sequence reads and identification of frameshift mutations and their protein products will occur through standard methods in the field. For sequence alignment, aligners specific for short or long reads can be used, e.g. BWA (Li and Durbin, Bioinformatics. 2009 Jul. 15; 25 (14): 1754-60) or Minimap2 (Li, Bioinformatics. 2018 Sep. 15; 34 (18): 3094-3100). Subsequently, frameshift mutations can be derived from the read alignments and their comparison to a reference genome sequence (e.g. the human reference genome GRCh37) using variant calling tools, for example Genome Analysis ToolKit (GATK), and the like (McKenna et al. Genome Res. 2010 September; 20 (9): 1297-303). The out-of-frame protein products (NOPs) resulting from frameshift mutations can be identified following the genetic triplet code known in the field and a database of reference sequences as publicly available through e.g. Ensembl, UCSC, NCBI or other sequence resources.

Preferably in step c) only the novel open reading frame is identified which corresponds to the same reading frame as the frame shift mutation identified in the patient that overlaps with or is adjacent to the frame shift location of the frame shifted gene to obtain candidate novel open reading frame sequences; Step d) can optionally be performed in case alternative splice constructs exist which overlap with the frame shift location, meaning the alternative splice construct would also be affected by the frame shift.

For practical reasons first a nucleic acid construct is generated, even if a peptide based vaccine is disclosed herein, however it is also disclosed herein that a peptide is directly synthesized in step e) based on the preceding steps. Therefore, alternatively step e) comprises combining each of the amino acid sequences encoded by the candidate open reading frame sequences and optionally by the candidate novel alternative splicing open reading frame sequences of the frame shift gene in a peptide.

In some preferred embodiment, in the method according to the invention multiple frame shift genes are identified in step b), and wherein candidate novel open reading frame sequences in step c), and optionally candidate novel alternative splicing open reading frame sequences in step d), for each of the frame shift genes identified in step b) are identified, and wherein the candidate open reading frame sequences and optionally the obtained candidate novel alternative splicing open reading frame sequences of the frame shift genes are combined in a single nucleotide construct or in separate nucleotide constructs for each frame shift gene.

In a preferred embodiment in step b) at least one gene is identified which is changed by a frame shift mutation in the tumor DNA and/or RNA of two or more patients in the cohort of cancer patients to obtain a frame shift gene.

In some preferred embodiment, in the method according to the invention, if candidate novel alternative splicing open reading frame sequences are identified, step e) further includes the step of reducing the amount of redundant overlapping sequence between corresponding candidate novel open reading frame sequences and candidate novel alternative splicing open reading frame sequences prior to combining the sequences in a nucleotide construct.

In some preferred embodiment, in the method according to the invention, in the combining of the sequences in step e) the sequences are directly linked adjacent to each other, or wherein between said sequences a linker nucleotide sequence may be present, preferably wherein between each of said sequences a linker nucleotide sequence is present, more preferably wherein said linker nucleotide sequences, independently, have a length of 3, 6, 9, 12 or 15 nucleotides, most preferably wherein each of said linker sequences has the nucleotide sequence GTAGATGAC.

The DNA and/or RNA for sequencing is preferably obtained by taking a sample from a tumor of the patient. The skilled person knowns how to obtain samples from a tumor of a patient and depending on the nature, for example location or size, of the tumor. Preferably the tumor is a solid tumor. Preferably the sample is obtained from the patient by biopsy or resection. The sample is obtained in such manner that is allows for sequencing of the genetic material obtained therein. In order to prevent a less accurate identification of at least one antigen, preferably the sequence of the tumor sample obtained from the patient is compared to the sequence of other non-tumor tissue of the patient, usually blood, obtained by known techniques (e.g. venipuncture).

Comparing of at least one sequence or portion thereof (i.e. part of the at least one sequence, preferably wherein the part is representative of at least 8 or 10 amino acids) from the set of sequences and a (DNA, RNA or peptide) sequence in the database can be done by any suitable mean available to the skilled person. Indeed the skilled person is well equipped with method to perform such comparison, for example using software tools like BLAST and the like.

Alternatively, a method is provided for generating a nucleic acid coding for a peptide, the method comprising the steps of:
  a) identifying frame shift mutations in the tumor DNA and/or RNA of a cohort of cancer patients in order to obtain a frame shift library;
  b) identifying at least two genes which are changed by a frame shift mutation in the tumor DNA and/or RNA of one or more patients in the cohort of cancer patients to obtain a frame shift gene;
  c) identifying each novel open reading frame in both the +1 and −1 reading frame that overlaps with or is adjacent to the frame shift location of the frame shifted gene to obtain candidate novel open reading frame sequences;
  d) optionally when present, identifying each novel open reading frames in both the +1 and −1 reading frame that overlaps with or is adjacent to the frame shift location for each alternative splicing construct of the frame shift gene to obtain candidate novel alternative splicing open reading frame sequences;
  e) combining at least two of the candidate open reading frame sequences and optionally the candidate novel alternative splicing open reading frame sequences of different frame shift genes in a nucleic acid construct.

In a preferred embodiment in step b) at least two genes are identified which are changed by a frame shift mutation in the tumor DNA and/or RNA of two or more patients in the cohort of cancer patients to obtain a frame shift gene.

Preferably in step c) only the novel open reading frame is identified which corresponds to the same reading frame as the frame shift mutation identified in the patient that overlaps with or is adjacent to the frame shift location of the frame shifted gene to obtain candidate novel open reading frame sequences;

Preferences, particularities and considerations expressed herein in the context of any other embodiment likewise apply to the above embodiment.

Indeed, it will be understood that all details, embodiments and preferences discussed with respect to one aspect of embodiment of the invention is likewise applicable to any other aspect or embodiment of the invention and that there is therefore not need to detail all such details, embodiments and preferences for all aspect separately.

Having now generally described the invention, the same will be more readily understood through reference to the following examples which is provided by way of illustration and is not intended to be limiting of the present invention. Further aspects and embodiments will be apparent to those skilled in the art.

EXAMPLES

The NEO-ORFeome is defined as all peptides encoded by the human genome that can be translated from +1 or −1 frame shifts of the coding sequences for all reference sequences (NCBI RefSeqs). These are named proto novel open reading frame peptides or pNOPs. Encountered STOP codons define borders or the translation products (ends a peptide and initiates a new one on the next amino acid)

The length of the translated peptide is ideally 10 or more amino acids. All isoforms are considered separately (every splice-variant).

From the NEO ORFeome, only pNOP regions that overlap with frame-shift mutations (n=2 or more) as defined in the TCGA cohort (n=10,186 patients spanning 33 cancer types) are considered, and selected. A visual representation is given in FIG. 3.

Figure 4:
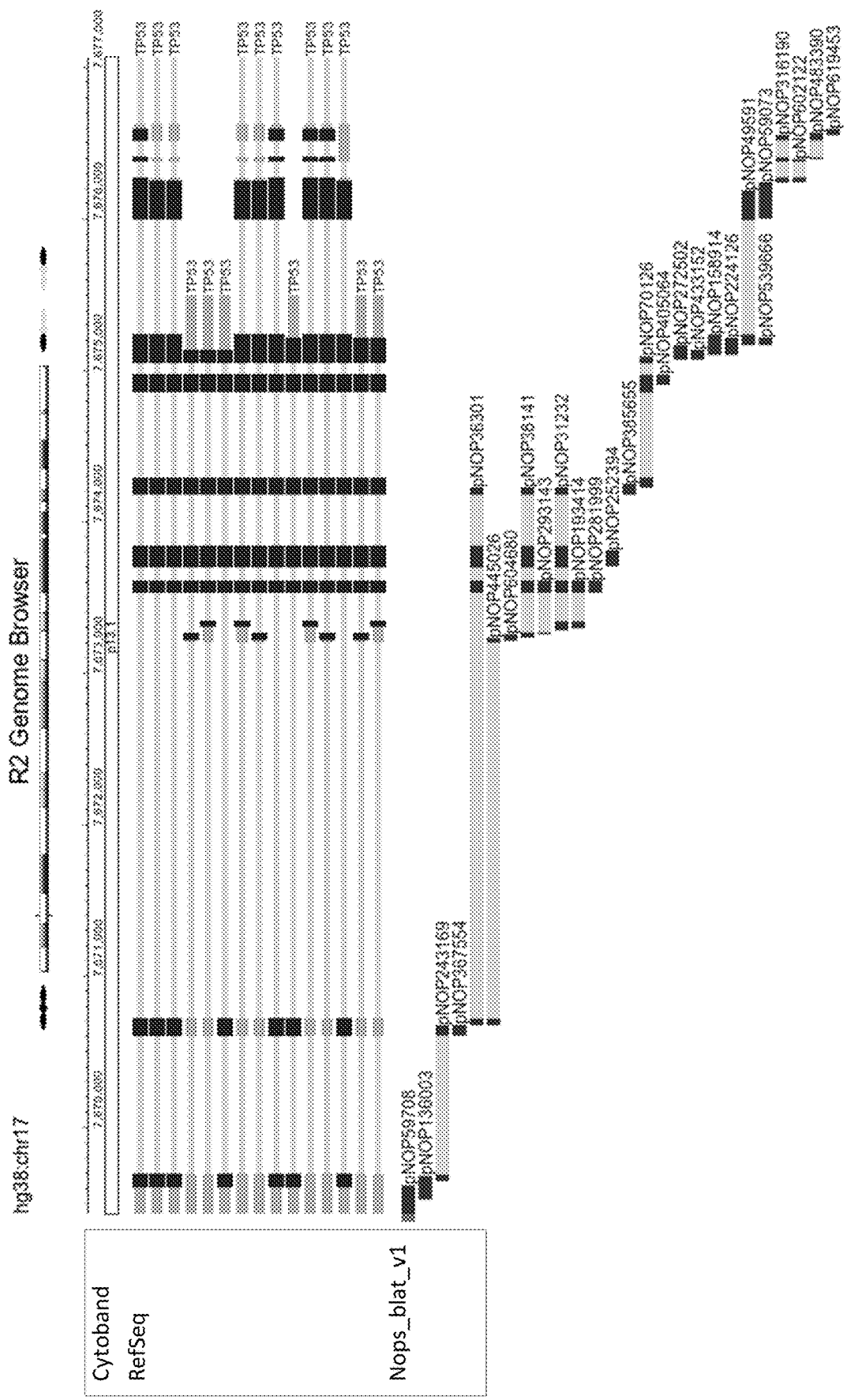
FIG. 4: Example graphical representation of for the splice variants of the gene TP53. The reference sequence (wild type, without mutations) is graphically displayed, together with alternative splice products.
Figure 5:
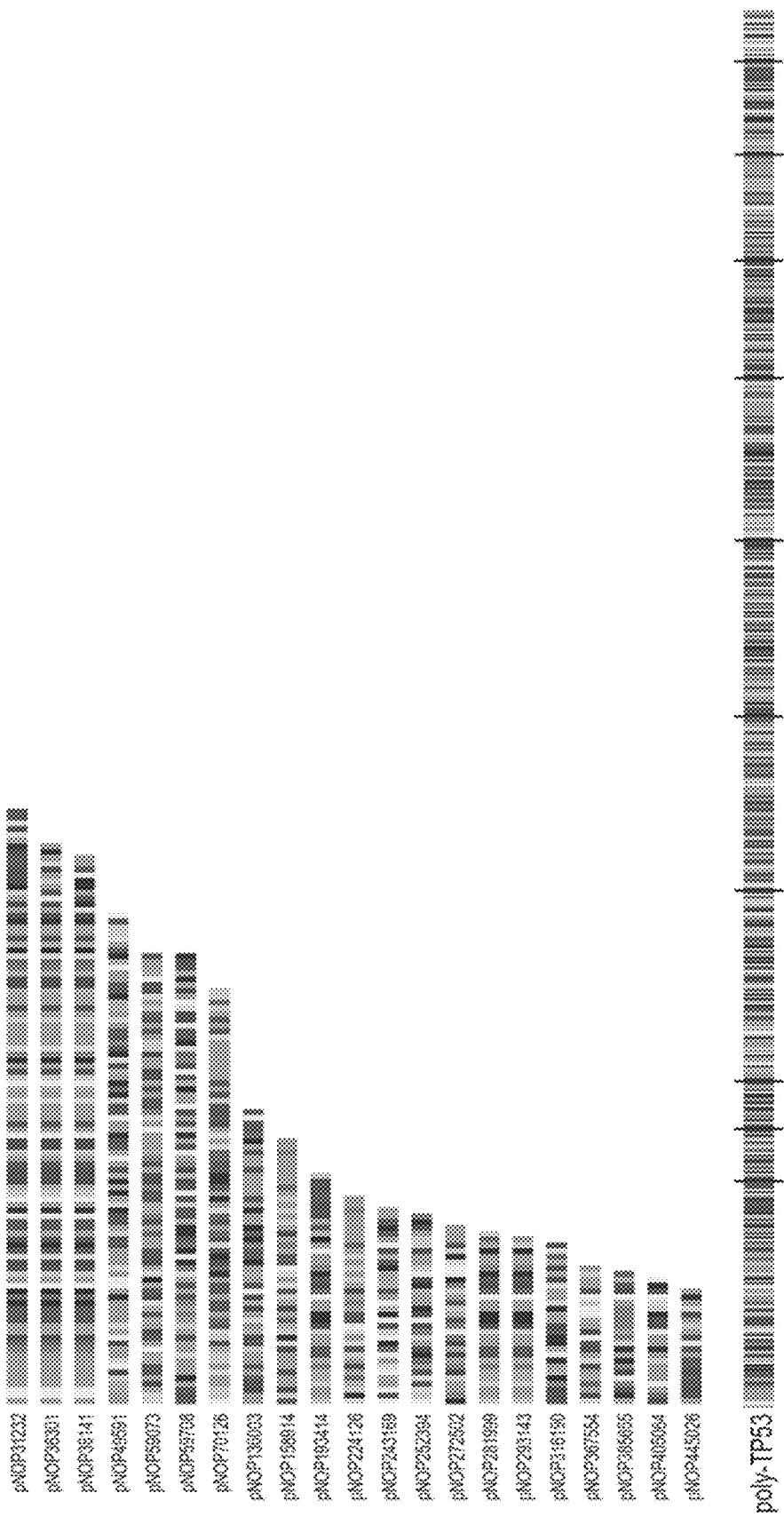
FIG. 5: Example graphical representation of a polyNOP peptide for the gene TP53. On the top all candidate NOPs overlapping with or adjacent to identified frame shift mutations in tumors from the TGCA patient cohort are listed for the gene TP51 and its splice variants. This list of NOPs include NOPs derived from splice variants and which also overlap or are adjacent to a frame shift mutation. Different shades of grey represent different amino acids in the peptides. On the bottom is a graphical representation of a polyNOP combining each of the NOP sequences such that the sequence of each individual NOP is represented in the polyNOP peptide, where sequence redundancy has been removed.

For each of these peptides thus selected we go back to the human genome sequence and define the largest possible open reading frame within the predicted spliced mRNA: it runs from the most upstream stop triplet that is in frame withe the peptide to the c-terminal stop triplet. As shown in FIGS. 4 and 5 result in the case of p53 in 21 open reading frames and corresponding peptides that are encoded by them. The complete list of such peptides (neo open reading frame peptides) and corresponding open reading frames (neo open reading frames) is collected.

All frame shift mutations defined in the TCGA cohort are superimposed on the remaining pNOPs and counted per gene (the collection of all isoforms), where a patient can be mentioned only once for any given gene (if a particular patient has more than 1 frame shift mutation in gene X, it still counts as 1 event). These patient counts per gene were then used to sort in descending order.

See Table 1. The first gene on the sorted list is the p53 gene (TP53), which has 21 neo-open reading frames peptides. These are encountered in 408 tumors/patients in the TCGA database. ARID1A: 229 patients, KMT2D: 160 patients, etc. Now these genes are ordered in a list of descending order of frequency. Starting with p53, the genes are ordered by the number of new patients they add to the group. Note that this is not necessarily the same as ordering by the total numbers of patients in the TCGA that have a neo open reading frame hit, since tumors may contain (and sometimes indeed do contain) hits in more than one gene. The listing in Table 1 orders by the largest number of new patients added. Potentially it is beneficial to have vaccines against more than one neo open reading frame peptide.

For each gene the following routine may be followed; all neo open reading frames as defined above are combined and linked into one polypeptide sequence for every gene separately. Any concatenation can be used for vaccine preparation. In this case we ordered them by the length, starting from the longest peptide, but that is not crucial, since for use as a vaccine for each patient in principle only one domain of the polypeptide is relevant. The peptides can be separated by a amino acid linker sequence. The thus defined polypeptide is then translated back into the encoding nucleotide sequence. In this case we used a table of the most often used and thus presumably most efficient triplet in cases where there is a choice. This defines one open reading frame. In FIGS. 4 and 5 it is illustrated how the p53 gene thus may result in an ORF and encoded protein of 850 triplets and amino acids. This polypeptide now contains all the neo open reading frame peptides encountered in 408 patients in the TCGA database.

Splice variants may be dealt with in the following way: the variant encoding the longest peptide that fulfills the criteria defined above is included in total, for additional splice variants the peptide sequence not encoded by the longest variant is added independently, making sure that we added at least 10 amino acids from the flanking sequence so that each potential epitope may be expected to be in the right context after proteasome trimming.

The list of genes as constructed above is cut off after 1103 genes; the lowest ranking gene on the list still adds 3 new patients based on the TCGA cohort.

Each gene in Table 1 is described by the list of amino acid sequences s that have gone into the fusion product, i.e. the peptide according to the invention. Note that their order within the encoding fusion gene is reasonably expected to be of little systematic effect on the efficacy of a vaccine.

The genes in the list described above can now be used to devise vaccines. Given their length it is assumed that in practice they may also be provided in the form of RNA, DNA or recombinant vectors.

Having now fully described this invention, it will be appreciated by those skilled in the art that the same can be performed within a wide range of equivalent parameters, concentrations, and conditions without departing from the spirit and scope of the invention and without undue experimentation.

All references cited herein, including journal articles or abstracts, published or corresponding patent applications, patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

SEQUENCE LISTING

The patent contains a lengthy sequence listing. A copy of the sequence listing is available in electronic form from the USPTO web site (https://seqdata.uspto.gov/?pageRequest=docDetail&DocID=US12391736B2). An electronic copy of the sequence listing will also be available from the USPTO upon request and payment of the fee set forth in 37 CFR 1.19(b)(3).

The invention claimed is:

1. A peptide comprising at least two amino acid sequences, wherein each of said at least two amino acid sequences is independently selected from the group consisting of SEQ ID NOS: 601 to 605, or an isolated nucleic acid comprising a nucleotide sequence encoding said peptide.

2. The peptide or isolated nucleic acid according to claim 1, wherein one of said at least two amino acid sequences is SEQ ID NO: 602, or a nucleic acid sequence encoding said peptide, and another of said at least two amino acid sequences is selected from the group consisting of SEQ ID NOS: 601, 603, 604, and 605, or an isolated nucleic acid comprising a nucleotide sequence encoding said peptide.

3. The peptide or isolated nucleic acid according to claim 2, wherein said at least two amino acid sequences comprise SEQ ID NO:602 and SEQ ID NO:601, or isolated nucleic acid sequences encoding said peptides.

\* \* \* \* \*